(12) United States Patent
Pflücker et al.

(10) Patent No.: US 6,903,134 B2
(45) Date of Patent: Jun. 7, 2005

(54) FORMULATION COMPRISING BENZOFURANONE DERIVATIVES FOR PROTECTION AGAINST OXIDATIVE STRESS

(75) Inventors: Frank Pflücker, Darmstadt (DE); Herwig Buchholz, Frankfurt (DE); Ralf Rosskopf, Muenster (DE); Joachim Bünger, Gross-Umstadt (DE)

(73) Assignee: Merck Patent GmbH, Darmstadt (DE)

( * ) Notice: Subject to any disclaimer, the term of this patent is extended or adjusted under 35 U.S.C. 154(b) by 71 days.

(21) Appl. No.: 10/182,385

(22) PCT Filed: Jan. 22, 2001

(86) PCT No.: PCT/EP01/00652
§ 371 (c)(1),
(2), (4) Date: Jul. 29, 2002

(87) PCT Pub. No.: WO01/55128
PCT Pub. Date: Aug. 2, 2001

(65) Prior Publication Data
US 2003/0060426 A1 Mar. 27, 2003

(30) Foreign Application Priority Data

Jan. 28, 2000 (DE) ......................................... 100 03 785
Oct. 11, 2000 (DE) ......................................... 100 50 237

(51) Int. Cl.$^7$ ........................ A61K 6/00; A61K 31/674; A61K 31/34; C07D 307/00
(52) U.S. Cl. ...................... 514/470; 514/461; 424/401; 424/78.03; 549/466
(58) Field of Search .......................... 549/466; 424/401, 424/78.03, 285; 514/461, 470

(56) References Cited

FOREIGN PATENT DOCUMENTS

| CH | 644603 A | 8/1984 |
|---|---|---|
| EP | 0113534 A | 7/1984 |

*Primary Examiner*—Sabiha Qazi
(74) *Attorney, Agent, or Firm*—Millen, White, Zelano, Branigan, P.C.

(57) ABSTRACT

The invention relates to a cosmetic or pharmaceutical formulation comprising at least one compound of formula (I). The cosmetics or pharmaceutical products are particularly suitable for the care of the skin in protecting against oxidative stress and ageing phenomena.

27 Claims, No Drawings

FORMULATION COMPRISING BENZOFURANONE DERIVATIVES FOR PROTECTION AGAINST OXIDATIVE STRESS

The present invention relates to cosmetic or pharmaceutical formulations and foods and food supplements which have improved protection against oxidation. The invention furthermore relates to novel compounds having antioxidative properties and to their use as antioxidants.

A certain degree of tanning of the skin is regarded in modern society as attractive and as an expression of vigour and sportiness. In addition to this desired action of the sun on the skin, a number of undesired side effects occur, such as sunburn or premature skin ageing and wrinkling. A number of effective UV filters have now been developed which, applied to the skin in the form of creams, lotions or gels, are able effectively to prevent the development of sunburn, even in the case of relatively great exposure to the sun. The UV filters present in the pharmaceutical or cosmetic preparation form a film or layer on the surface of the skin and do not penetrate into deeper skin layers with further care substances present in the preparation. Known UV filters and sunscreens thus only act by absorbing certain regions of the sunlight, preventing this radiation from penetrating into deeper layers of the skin. As is known, the most dangerous part of solar radiation is formed by ultraviolet rays having a wavelength of less than 400 nm. The lower limit for the ultraviolet rays which reach the earth's surface is restricted to about 280 nm by absorption in the ozone layer. The sun-protection filters usual today in cosmetics absorb in a wavelength range from 280 to 400 nm. This range covers UV-B rays having a wavelength of between 280 and 320 nm, which play a crucial role in the formation of solar erythema, and also UV-A rays, having a wavelength of between 320 and 400 nm, which tan the skin, but also allow ageing, favour the triggering of an erythematous reaction or can exacerbate this reaction in certain people or even trigger phototoxic or photoallergic and irritative reactions.

Skin damage is not caused just by sunlight, but also by other external influences, such as cold or heat. Furthermore, the skin undergoes natural ageing, with the formation of wrinkles and a reduction in the elasticity of the skin.

The object of care cosmetics is wherever possible to obtain the impression of youthful skin. In principle, there are various ways of achieving this object. For example, existing skin damage, such as irregular pigmentation or the development of wrinkles, can be compensated for by covering powders or creams. Another approach is to protect the skin against environmental influences which lead to permanent damage and thus ageing of the skin. The idea is therefore to intervene in a preventative manner and thus to delay the ageing process. One example of this is the UV filters already mentioned, which, as a result of absorption of certain wavelength ranges, prevent or at least reduce skin damage. Whereas in the case of UV filters the damaging event, the UV radiation, is screened off by the skin, another route involves attempting to support the skin's natural defence or repair mechanisms against the damaging event. Finally, a further approach involves compensating for the weakening defence functions of the skin against harmful influences with increasing age by externally supplying substances which are able to replace this diminishing defence or repair function. For example, the skin has the ability to scavenge free radicals formed by external or internal stress factors. This ability diminishes with increasing age, causing the ageing process to accelerate with increasing age.

It must be possible for substances which are intended to support or replace defence or repair functions of the skin to be transported to their site of action. Two methods are in principle available for this purpose: either the substance is applied to the skin and penetrates through the outer layers into deeper layers of the skin or the active ingredient is, for example after oral intake, transported to the site of action via the bloodstream.

A further difficulty in the preparation of cosmetics is that active ingredients which are intended to be incorporated into cosmetic formulations are frequently unstable and can be damaged in the formulation. The damage may be caused, for example, by a reaction with atmospheric oxygen or by absorption of UV rays. The molecules damaged in this way may, for example, change their colour and/or lose their activity through their structural change.

DE 197 10 854 A1 describes the use of benzophenones and their derivatives against UV-induced decomposition of dibenzoylmethane and its derivatives.

DE 197 46 654 A1 describes cosmetic and pharmaceutical preparations comprising photostable UV filters. 4,4-Diarylbutadienes are used here as photostable UV filters in cosmetic and pharmaceutical preparations for protecting the human skin or human hair against sunlight, alone or together with compounds which absorb in the UV region and which are known per se for cosmetic and pharmaceutical preparations.

DE 195 08 608 A1 describes a light-stable cosmetic composition. Cosmetic compositions are disclosed for protection against UV rays having a wavelength of between 280 and 400 nm which comprise at least one tetraalkylquercetin in a cosmetically acceptable, oil-based medium.

DE 197 55 504 A1 describes the use of flavones and flavonoids against UV-induced decomposition of dibenzoylmethane and its derivatives.

DE 197 50 030 A1 describes a cosmetic preparation comprising butylmethoxydibenzoylmethane as light-protection filter. In order to improve the photostability, insoluble inorganic particles which absorb in the UVA region are added to the cosmetic preparation. The insoluble inorganic particles used are microfine particles selected from the group consisting of titanium dioxide, iron oxide, cerium oxide and zinc oxide.

U.S. Pat. No. 4,532,257 describes substituted coumaranones in which the benzofuran moiety is either unsubstituted or carries a carboxyl group and an alkyl or alkenyl group. Various substituents are described for the benzyl group. The compounds are proposed as antiallergic or antiinflammatory active ingredients, in particular for the treatment of asthma.

GB 2,131,431 describes coumaranone derivatives which may be substituted, inter alia, by $C_{1-4}$-alkoxy groups. The compounds are likewise proposed for the treatment of allergic or inflammatory diseases.

WO 91/17749 proposes growth inhibitors for the treatment of cancer. Amongst the compounds proposed are aurones, in which the basic skeleton may be substituted by hydroxyl or methoxy groups.

FR 1 502 727 describes the preparation of aryl-2-amino-3-benzofuran and of aryl-2-benzo-3(2H)-furanone.

The object of the invention is therefore to provide a cosmetic or pharmaceutical composition which has a protective action against UV rays and/or exerts a protective action against oxidative stress on body cells and/or counters ageing of the skin.

This object is achieved by a cosmetic or pharmaceutical formulation comprising at least one compound of the formula I

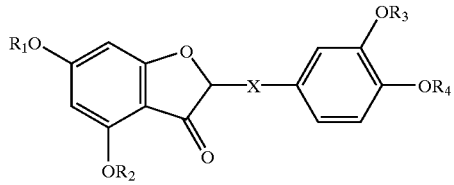

in which —X— is a single bond, —CH$_2$—, =CH—, —C(O)—, =C(OR$^5$)—, —C(NR$^5$)—, —CH(NR$^5$R$^6$)— or —CH(OR$^5$)—, and R$^1$, R$^2$, R$^3$, R$^4$, R$^5$ and R$^6$ may be identical or different and are, independently of one another,

H straight-chain or branched C$_1$- to C$_{12}$-alkyl and/or alkylcarbonyl groups, straight-chain or branched C$_3$- to C$_{12}$-alkenyl and/or -alkenylcarbonyl groups, straight-chain or branched C$_1$- to C$_{12}$-hydroxyalkyl groups, in which the hydroxyl group may be bonded to a primary or secondary carbon atom of the chain, and furthermore the alkyl chain may also be interrupted by oxygen, C$_3$- to C$_{10}$-cycloalkyl and/or cycloalkylcarbonyl groups and C$_3$- to C$_{12}$-cycloalkenyl and/or cycloalkenylcarbonyl groups, in which each of the rings may also be bridged by —(CH$_2$)$_n$— groups, where n=from 1 to 3, aryl and/or arylcarbonyl groups, heteroaryl and/or heteroarylcarbonyl groups, where these groups may be substituted by alkyl, hydroxyl, alkoxy, amino, mono- and di-alkylamino, sulfonic acid, carboxyl and/or halogen groups, mono- and/or oligoglycosyl radicals,

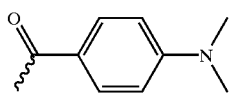
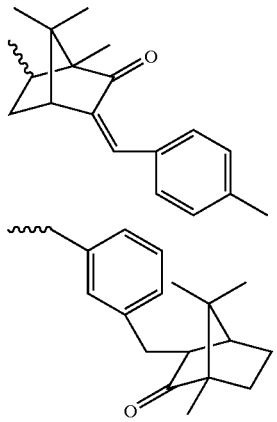
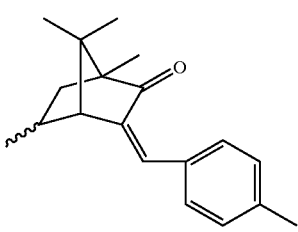
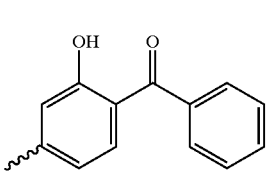
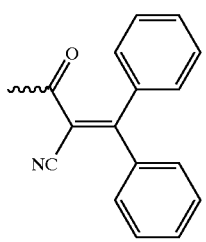

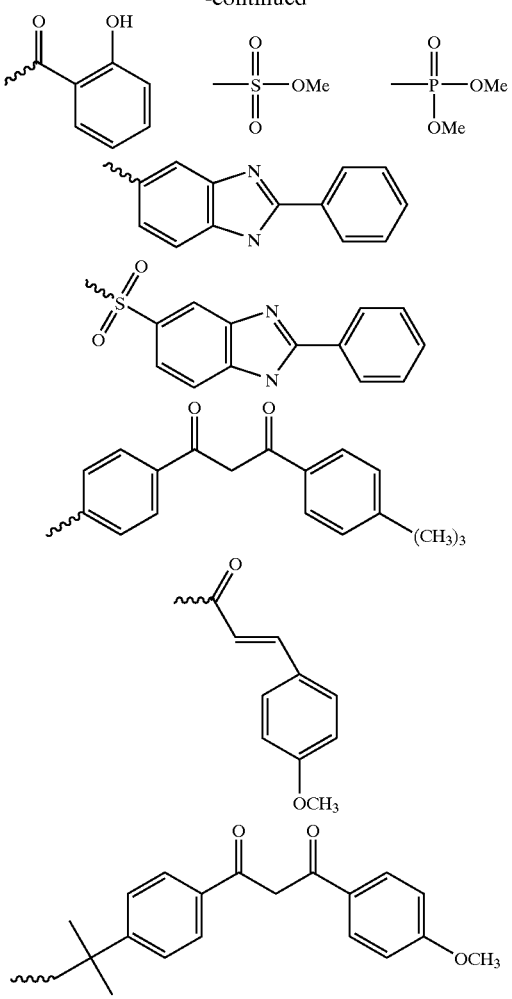

in which Me is a proton or an alkali metal ion, in particular a sodium or potassium ion.

The radicals may thus be bonded to the basic structure as ethers or as esters.

The positive action of the cosmetic or pharmaceutical preparation according to the invention is presumably based on the action of the compounds of the formula I as antioxidants or as free-radical scavengers. In order to be able to develop their positive action on the skin, it should be possible for the compounds of the formula I to penetrate into deeper skin layers. A number of possibilities are available for this purpose. Firstly, the compounds of the formula I may have adequate lipophilicity in order to be able to penetrate the outer skin layer into epidermal layers. As a further possibility, corresponding transport agents, for example liposomes, which facilitate transport of the compounds of the formula I through the outer skin layers, may also be provided in the preparation. Finally, systemic transport of the compounds of the formula I is also conceivable. In this case, the preparation is designed in such a way, for example, that it is suitable for oral administration.

In general, the substances of the formula I act as free-radical scavengers. Free radicals of this type are not only produced by sunlight, but are also formed under various conditions. Examples are anoxia, which blocks the electron flow upstream of the cytochrome oxidases and causes the formation of superoxide free-radical anions; inflammation which is associated, inter alia, with the formation of superoxide anions by the membrane NADPH oxidase of the leukocytes, but which is also associated with the formation (by disproportionation in the presence of iron(II) ions) of the hydroxyl free radicals and other reactive species which are normally involved in the phenomenon of phagocytosis; and lipid autooxidation, which is generally initiated by a hydroxyl free radical and produces lipidic alkoxy free radicals and hydroperoxides.

It is assumed that the compounds of the formula I also act as enzyme inhibitors. They are thought to inhibit histidine decarboxylase, protein kinases, elastase, aldose reductase and hyaluronidase, and therefore enable the intactness of the basic substance of vascular sheaths to be maintained. Furthermore, they are thought to inhibit catechol O-methyltransferase in a non-specific manner, increasing the amount of available catecholamines and thus the vascular strength. Furthermore, they inhibit AMP phosphodiesterase, providing the substances with potential for inhibiting thrombocyte aggregation.

Owing to these properties, the formulations according to the invention or the compounds according to the invention are generally suitable for immunoprotection and for DNA and RNA protection. In particular, the formulations and compounds are suitable for protecting DNA and RNA against oxidative attacks, against free radicals and against damage by radiation, in particular UV radiation. A further advantage of the formulations according to the invention and the compounds according to the invention is cell protection, in particular protection of Langerhans cells, against damage by the above-mentioned influences. All these uses are expressly also a subject-matter of the present invention.

For the purposes of the invention, preference is given to cosmetic or pharmaceutical formulations which comprise compounds of the formula I in which —X— is a single bond, —CH$_2$—, —C(O)—, =C(OR$^5$)—, —C(NR$^5$)—, —CH(NR$^5$R$^6$)— or —CH(OR$^5$)—.

Preference is furthermore given to cosmetic or pharmaceutical formulations which comprise compounds of the formula I in which —X—is =CH— and at least one radical from R$^1$, R$^2$, R$^3$ and R$^4$ is a group selected from the following list:

straight-chain or branched C$_1$- to C$_{12}$-alkylcarbonyl groups, straight-chain or branched C$_3$- to C$_{12}$-alkenylcarbonyl groups, straight-chain or branched C$_1$- to C$_{12}$-hydroxyalkyl groups, in which the hydroxyl group may be bonded to a primary or secondary carbon atom of the chain, and furthermore the alkyl chain may also be interrupted by oxygen, C$_3$- to C$_{10}$-cycloalkylcarbonyl groups and C$_3$- to C$_{12}$-cycloalkenyl and/or cycloalkenylcarbonyl groups, in which each of the rings may also be bridged by —(CH$_2$)$_n$— groups, where n=from 1 to 3, aryl and/or arylcarbonyl groups, heteroaryl and/or heteroarylcarbonyl groups, where these groups may be substituted by alkyl, hydroxyl, alkoxy, amino, mono- and di-alkylamino, sulfonic acid, carboxyl and/or halogen groups, mono- and/or oligoglycosyl radicals,

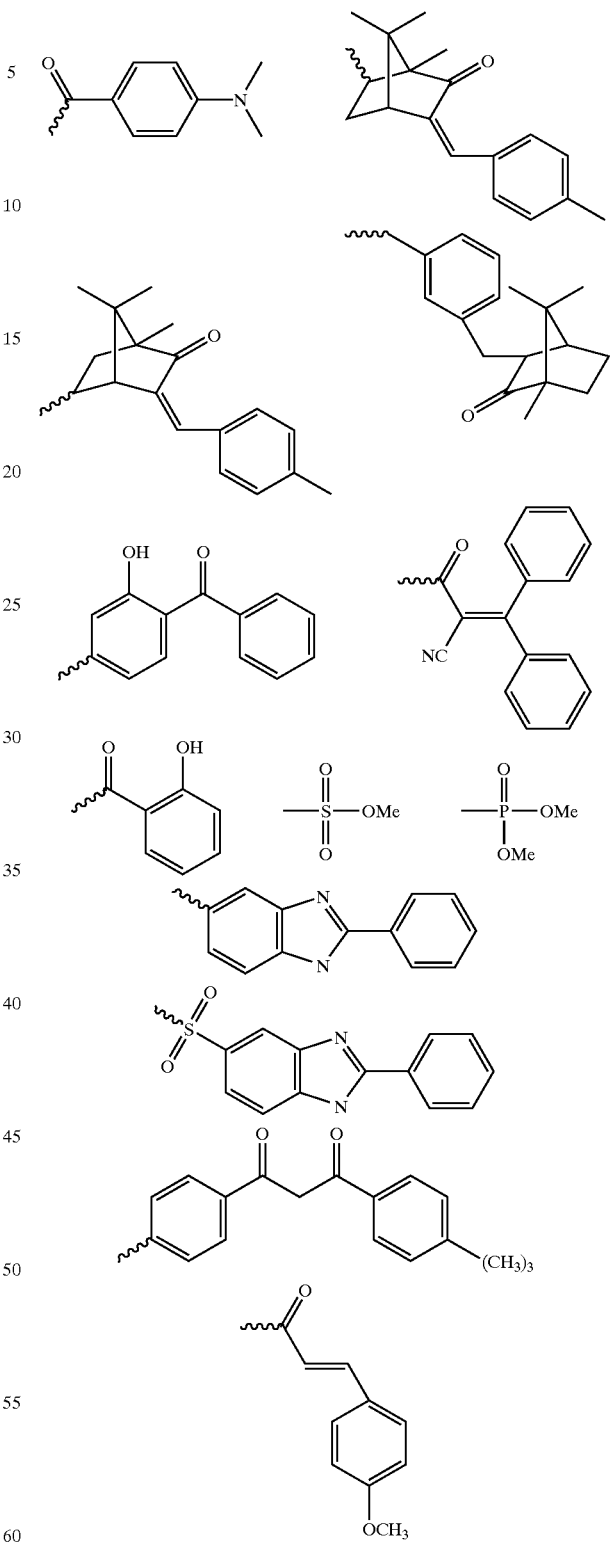

in which Me is a proton or an alkali metal ion, in particular a sodium or potassium ion.

The basic structure 4,6,3',4'-tetrahydroxybenzylcoumaran-3-one has very good properties. This corresponds to the compound of the formula I in which X=—CH$_2$— and R$^1$=R$^2$=R$^3$=R$^4$=H. The potential of this compound as antioxidant and free-radical scavenger, in particular when used in cosmetics, pharmaceuticals and foods, has not been recognised hitherto. This also applies to 4,6,3',4'-tetrahydroxyaurone, which corresponds to a compound of the formula I in which X==CH—, and $R^1=R^2=R^3=R^4=H$. This opens up the route to a new class of antioxidants which arises through variation of the substituents $R^1$, $R^2$, $R^3$ and $R^4$. Thus, for example, the solubility in water or oils can be matched to the respective need by replacing one or more protons in the hydroxyl groups of the basic structures by, for example, alkyl groups, cycloalkyl groups or -alkenyl groups. These substituents may in turn be modified in their properties by substituents, such as, for example, hydroxyl groups or amino groups, which may in turn be alkylated. The solubility in water may be improved by, for example, selecting the radicals $R^1$, $R^2$, $R^3$ and $R^4$ as sulfate or phosphate groups. A mixture of mono-, di- and trisulfate, referred to below as "sulfated coumaranone", is particularly suitable. Particular emphasis is placed on the trisulfate (X=—$CH_2$—; $R^1=R^3=R^4=SO_3Me$, $R^2=H$), which is represented by the following formula:

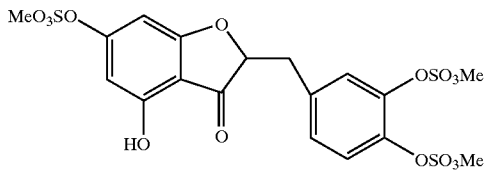

The oil solubility can be improved by, for example, esterifying the hydroxyl groups of the basic structures using ethylhexanecarboxylic acid.

Further suitable radicals are obtained by esterification with monocarboxylic acids, such as butyric acid, valeric acid, hexanoic acid, sorbic acid, ascorbic acid or lauric acid. These radicals promote transport of the compound through biological membranes. The basic structure can then be liberated in the cell by cleaving off the carboxylic acids by means of esterases.

A further particularly interesting class of compounds arises if the basic structures, which here are preferably taken to mean the basic structures in which X is a single bond, —$CH_2$— or =CH—, and $R^1=R^2=R^3=R^4$=H, are substituted by UV-absorbent groups. The compounds and formulations comprising these compounds then advantageously exhibit a protective action as antioxidants and as UV filters. Even the basic structures exhibit a protective action against UVA radiation. By means of suitable radicals $R^1$, $R^2$, $R^3$ and $R^4$, UVA/B broad-band filters can therefore be provided.

The groups here are advantageously selected in such a way that they exhibit, in particular, an absorption maximum in the wavelength ranges of UVA and UVB radiation which are particularly harmful for the skin. The UV-B content of sunlight covers the range from 280 to 320 nm and UV-A radiation covers the range >320 nm, which is directly adjacent to the region of visible light.

Preference is also given to structures in which at least one of the radicals $R^1$, $R^2$, $R^3$ and $R^4$ is formed by a mono- or oligosaccharide. Preference is given here to hexosyl radicals, in particular ramnosyl radicals and glycosyl radicals. However, other hexosyl radicals, for example allosyl, altrosyl, galactosyl, gulosyl, idosyl, mannosyl and talosyl, may also advantageously be used. It may also be advantageous to use pentosyl radicals. The glycosyl radicals may be linked to the basic structure by means of an α- or β-glycosidic link. A preferred disaccharide is, for example, 6-O-(6-deoxy-α-L-mannopyranosyl)-β-D-glucopyranoside.

Aurone ($R^1=R^2=R^3=R^4$=H, X==CH—) belongs to the class of the bioflavonoids. The term bioflavonoids here is taken to mean naturally occurring flavonoids.

4,6,3',4'-tetrahydroxybenzylcoumaran-3-one is accessible, for example, from quercetin by reaction of quercetin with sodium dithionite in aqueous solution. It differs from bioflavonoids through the five-membered ring of the benzofuranone.

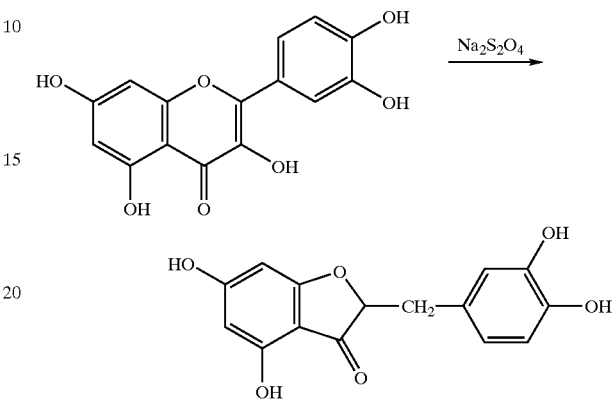

Another way of preparing 4,6,3',4'-tetrahydroxybenzylcoumaran-3-one proceeds, as described in British Patent GB 2,131,431, via aurone. Aurone can also be prepared synthetically here. This is described, for example, in British Patent GB 2,030,142.

Variation of the group designated by X in the formula I gives rise to a broader area of compounds. Through incorporation of a carbonyl group —C(O)—, the wavelength of the UV absorption can be modified. Through incorporation of a hydroxyl or amino function, further linkage points, for example, are available for modification of the compounds of the formula I.

The formulations according to the invention usually comprise the compound of the formula I in amounts of 0.01–10% by weight. These amounts ensure that the compound of the formula I results in the formulation according to the invention having the stated properties. If particular requirements are to be made of the formulation, however, the formulation may also comprise the compound of the formula I in differing amounts. It is particularly preferred for the compound of the formula I to be present in the formulations according to the invention in amounts of 0.02–5% by weight, with formulations comprising 0.05–0.2% by weight of the compound of the formula I having proven particularly advantageous.

The protective action against UV radiation can be improved if the formulation comprises one or more UV filters.

In principle, all UV filters are suitable for a combination. Particular preference is given to UV filters whose physiological acceptability has already been demonstrated. There are many proven substances which are known from the specialist literature both for UVA and UVB filters, for example benzylidenecamphor derivatives, such as
3-(4'-methylbenzylidene)-dl-camphor (for example Eusolex® 6300),
3-benzylidenecamphor (for example Mexoryl® SD),
polymers of N-{(2 and 4)-[(2-oxoborn-3-ylidene)methyl] benzyl}acrylamide (for example Mexoryl® SW),
N,N,N-trimethyl-4-(2-oxoborn-3-ylidenemethyl)anilinium methylsulfate (for example Mexoryle® SK) or α-(2-oxoborn-3-ylidene)toluene-4-sulfonic acid (for example Mexoryl® SL),
benzoyl- or dibenzoylmethanes, such as
1-(4-tert-butylphenyl)-3-(4-methoxyphenyl)propane-1,3-dione (for example Eusolex® 9020) or
4-isopropyldibenzoylmethane (for example Eusolex® 8020),
benzophenones, such as
2-hydroxy-4-methoxybenzophenone (for example Eusolex® 4360) or
2-hydroxy-4-methoxybenzophenone-5-sulfonic acid and its sodium salt (for example Uvinul® MS-40),
methoxycinnamic acid esters, such as
octyl methoxycinnamate (for example Eusolex® 2292),
isopentyl 4-methoxycinnamate, for example as a mixture of the isomers (for example Neo Heliopan® E 1000),
salicylate derivatives, such as
2-ethylhexyl salicylate (for example Eusolex® OS),
4-isopropylbenzyl salicylate (for example Megasol®) or
3,3,5-trimethylcyclohexyl salicylate (for example Eusolex® HMS),
4-aminobenzoic acid and derivatives, such as
4-aminobenzoic acid,
2-ethylhexyl 4-(dimethylamino)benzoate (for example Eusolex® 6007),
ethoxylated ethyl 4-aminobenzoate (for example Uvinul® P25),
and further substances, such as
2-ethylhexyl 2-cyano-3,3-diphenylacrylate (for example Eusolex® OCR),
2-phenylbenzimidazole-5-sulfonic acid and its potassium, sodium and triethanolamine salts (for example Eusolex® 232),
3,3'-(1,4-phenylenedimethylene)bis(7,7-dimethyl-2-oxobicyclo[2.2.1]-hept-1-ylmethanesulfonic acid and its salts (for example Mexoryl® SX) and
2,4,6-trianilino-(p-carbo-2'-ethylhexyl-1'-oxy)-1,3,5-triazine (for example Uvinul® T 150).

The compounds mentioned in the list should only be regarded as examples. It is of course also possible to use other UV filters.

These organic UV filters are generally incorporated into cosmetic formulations in an amount of from 0.5 to 10 per cent by weight, preferably 1–8%.

Further suitable organic UV filters are, for example,
2-(2H-benzotriazol-2-yl)4-methyl-6-(2-methyl-3-(1,3,3,3-tetramethyl-1-(trimethylsilyloxy)disiloxanyl)propyl)phenol (for example Silatrizole®),
2-ethylhexyl 4,4'-[(6-[4-((1,1-dimethylethyl)aminocarbonyl)phenyl-amino]-1,3,5-triazine-2,4-diyl)diimino]bis(benzoate) (for example Uvasorb® HEB),
α-(trimethylsilyl)-ω-[trimethylsilyl)oxy]poly[oxy(dimethyl [and approximately 6% of methyl[2-[p-[2,2-bis (ethoxycarbonyl)vinyl]phenoxy]-1-methyleneethyl] and approximately 1.5% of methyl[3-[p-[2,2-bis (ethoxycarbonyl)vinyl]phenoxy]propenyl] and from 0.1 to 0.4% of (methylhydrogen]silylene]](n≈60) (CAS No. 207 574-74-1)
2,2'-methylenebis(6-(2H-benzotriazol-2-yl)-4-(1,1,3,3-tetramethylbutyl)-phenol) (CAS No. 103 597-45-1)
2,2'-(1,4-phenylene)bis(1H-benzimidazole-4,6-disulfonic acid, monosodium salt) (CAS No. 180 898-37-7) and
2,4-bis{[4-(2-ethylhexyloxy)-2-hydroxy]phenyl}-6-(4-methoxyphenyl)-1,3,5-triazine (CAS No. 103 597-45-, 187 393-00-6).

These organic UV filters are generally incorporated into cosmetic formulations in an amount of from 0.5 to 20 per cent by weight, preferably 1–15%.

Conceivable inorganic UV filters are those from the group consisting of titanium dioxides, such as, for example, coated titanium dioxide (for example Eusolex® T-2000, Eusolex® T-AQUA), zinc oxides (for example Sachtotec®), iron oxides and also cerium oxides. These inorganic UV filters are generally incorporated into cosmetic formulations in an amount of from 0.5 to 20 per cent by weight, preferably 2–10%.

Preferred compounds having UV-filtering properties are 3-(4'-methylbenzylidine)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and its potassium, sodium and triethanolamine salts.

The protective action against the damaging effects of UV radiation can be optimised by combining one or more compounds of the formula I with further UV filters.

The combination of the above-mentioned UV filters with a compound of the formula I in a formulation then gives rise to a composition which combines light protection with particular skin friendliness. The combination of UV filters with compounds of the formula I in compositions of this type usually takes place in ratios in the range from 100 000:1 to 1:10, preferably in amounts of from 1000:1 to 1:10.

The protective action against oxidative stress or against the effect of free radicals can be further improved if the formulation comprises one or more further antioxidants.

There are many proven substances known from the specialist literature which can be used, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylidineglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Mixtures of antioxidants are likewise suitable for use in the cosmetic formulations according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with compounds of the formula I in compositions of this type in ratios in the range from 1000:1 to 1:1000, preferably in amounts of from 100:1 to 1:100.

The formulations according to the invention may comprise vitamins as further ingredients. The cosmetic formulations according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B$_1$), riboflavin (vitamin B$_2$), nicotinamide, vitamin C (ascorbic acid), vitamin D, ergocalciferol (vitamin D$_2$), vitamin E, DL α-tocopherol, tocopherol E acetate, tocopherol hydrogen-succinate, vitamin K$_1$, esculin (vitamin P active ingredient), thiamine (vitamin B$_1$), nicotinic acid (niacin), pyridoxine, pyridoxal, pyridoxamine, (vitamin B$_6$), panthothenic acid, biotin, folic acid and cobalamine (vitamin B$_{12}$), particularly preferably vitamin A palmitate, vitamin C, DL-α-tocopherol, tocopherol E acetate, nicotinic acid, panthothenic acid and biotin. Vitamins are usually employed here with compounds of the formula I in ratios in the range from 1000:1 to 1:1000, preferably in amounts of from 100:1 to 1:100.

The formulations according to the invention may in addition comprise further conventional skin-protecting or skin-care active ingredients. These may in principle be any active ingredients known to the person skilled in the art.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., *Eur. J. Biochem.*, 149 (1985) pages 135–139). Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and their derivatives. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be employed in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacteria cells.

Pharmaceutical products, such as non-glycosylated, pharmaceutically active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European Patent Application EP-A-0 671 161 describes, in particular, that ectoin and hydroxyectoin are employed in cosmetic preparations, such as powders, soaps, surfactant-containing cleansing products, lipsticks, rouge, make-ups, care creams and sunscreen preparations.

Preference is given here to the use of a pyrimidinecarboxylic acid of the following formula II

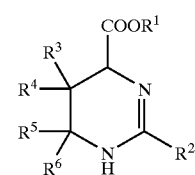

in which R$^1$ is a radical H or C1–8-alkyl, R$^2$ is a radical H or C1–4-alkyl, and R$^3$, R$^4$, R$^5$ and R$^6$ are each, independently of one another, a radical from the group consisting of H, OH, NH$_2$ and C1–4-alkyl. Preference is given to the use of pyrimidinecarboxylic acids in which R$^2$ is a methyl or ethyl group, and R$^1$ or R$^5$ and R$^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). The formulations according to the invention preferably comprise pyrimidinecarboxylic acids of this type in amounts of up to 15% by weight. The pyrimidinecarboxylic acids are preferably employed here in ratios of from 100:1 to 1:100 with respect to the compounds of the formula 1, with ratios in the range from 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Preparations which comprise 2-hydroxy-5-methyllaurophenone oxime are accordingly suitable for the treatment of skin diseases which are accompanied by inflammation. It is known that preparations of this type can be used, for example, for the therapy of psoriasis, various forms of eczema, irritative and toxic dermatitis, UV dermatitis and further allergic and/or inflammatory diseases of the skin and integumentary appendages. Formulations according to the invention which, in addition to the compound of the formula I, additionally comprise an aryl oxime, preferably 2-hydroxy-5-methyllaurophenone oxime, exhibit surprising antiinflammatory suitability. The formulations here preferably comprise from 0.01 to 10% by weight of the aryl oxime, it being particularly preferred for the preparation to comprise from 0.05 to 5% by weight of aryl oxime.

All compounds or components which can be used in the formulations are either known or are commercially available or can be synthesised by known processes.

The one or more compounds of the formula I can be incorporated into cosmetic formulations in the customary manner. Suitable formulations are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the cosmetic or pharmaceutical food supplement formulations according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any desired customary excipients, auxiliaries and, if desired, further active ingredients may be added to the formulation.

Preferred auxiliaries originate from the group consisting of preservatives, antioxidants, stabilisers, solubilisers, vitamins, colorants and odour improvers.

Ointments, pastes, creams and gels may comprise the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary excipients, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary excipients, such as solvents, solubility promoters and emulsifiers, for example water, ethanol, isopropanol, ethyl carbonate, ethyl acetate, benzyl alcohol, benzyl benzoate, propylene glycol, 1,3-butylglycol, oils, in particular cottonseed oil, peanut oil, wheatgerm oil, olive oil, castor oil and sesame oil, glycerol fatty acid esters, polyethylene glycols and fatty acid esters of sorbitan or mixtures of these substances.

Suspensions may comprise the customary excipients, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar agar and tragacanth, or mixtures of these substances.

Soaps may comprise the customary excipients, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary excipients, such as salts of fatty alcohol sulfates, fatty alcohol ether sulfates, sulfosuccinic monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary excipients, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic application forms are also lipsticks, lipcare sticks, mascara, eyeliner, eyeshadow, rouge, powder make-up, emulsion make-up and wax make-up, and sunscreen, presun and aftersun preparations.

The preferred preparation forms according to the invention include, in particular, emulsions.

Emulsions according to the invention are advantageous and comprise, for example, the said fats, oils, waxes and other fatty substances, as well as water and an emulsifier, as usually used for a formulation of this type.

The lipid phase may advantageously be selected from the following group of substances:

mineral oils, mineral waxes, oils, such as triglycerides of capric or caprylic acid, furthermore natural oils, such as, for example, castor oil, fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids, silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group consisting of esters of aromatic carboxylic acids and saturated and/or unsaturated, branched and/or unbranched alcohols having a chain length of from 3 to 30 carbon atoms. Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group consisting of branched and unbranched hydrocarbons and waxes, silicone oils, dialkyl ethers, the group consisting of saturated or unsaturated, branched or unbranched alcohols, and fatty acid triglycerides, specifically the triglycerol esters of saturated and/or unsaturated, branched and/or unbranched alkanecarboxylic acids having a chain length of from 8 to 24, in particular 12–18, carbon atoms. The fatty acid triglycerides may advantageously be selected, for example, from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate and of cyclomethicone and 2-ethylhexyl isostearate.

The aqueous phase of the preparations according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group consisting of silicon dioxide, aluminium silicates, polysaccharides or derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the formulations according to the invention comprise hydrophilic surfactants.

The hydrophilic surfactants are preferably selected from the group consisting of the alkyl glycosides, acyl lactylates, betaines and coconut amphoacetates.

The alkyl glycosides are themselves advantageously selected from the group consisting of the alkyl glycosides that are distinguished by the structural formula $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

where R is a branched or unbranched alkyl radical having from 4 to 24 carbon atoms, and where $\overline{DP}$ denotes a mean degree of glycosidation of up to 2.

The value $\overline{DP}$ represents the degree of glycosidation of the alkyl glycosides used in accordance with the invention and is defined as

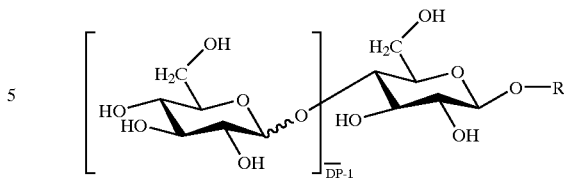

in which $p_1, p_2, p_3 \ldots p_i$ represent the proportion of mono-, di-, tri- . . . i-glycosylated products in per cent by weight. Advantageous according to the invention are products having degrees of glycosylation of 1-2, particularly advantageously of from 1.1 to 1.5, very particularly advantageously of 1.2–1.4, in particular of 1.3.

The value $\overline{DP}$ takes into account the fact that alkyl glycosides are generally, as a consequence of their preparation, in the form of mixtures of mono- and oligoglycosides. A relatively high content of monoglycosides, typically in the order of 40–70% by weight, is advantageous in accordance with the invention.

Alkyl glycosides which are particularly advantageously used for the purposes of the present invention are selected from the group consisting of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active ingredients used in accordance with the invention, for example Plantaren® 1200 (Henkel KGaA), Oramix® NS 10 (Seppic).

The acyl lactylates are themselves advantageously selected from the group consisting of the substances which are distinguished by the structural formula

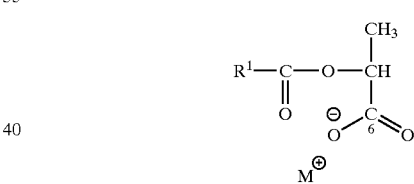

where $R^1$ is a branched or unbranched alkyl radical having from 1 to 30 carbon atoms, and $M^+$ is selected from the group consisting of the alkali metal ions and the group consisting of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formula

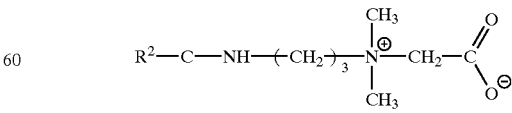

where $R^2$ is a branched or unbranched alkyl radical having from 1 to 30 carbon atoms.

$R^2$ is particularly advantageously a branched or unbranched alkyl radical having from 6 to 12 carbon atoms.

For example, capramidopropylbetaine, for example the product Tego® Betain 810 from Th. Goldschmidt AG, is advantageous.

A coconut amphoacetate which is advantageous for the purposes of the invention is, for example, sodium coconut amphoacetate, as available under the name Miranol® Ultra C32 from Miranol Chemical Corp.

The preparations according to the invention are advantageously characterised in that the hydrophilic surfactant(s) is (are) present in concentrations of 0.01–20% by weight, preferably 0.05–10% by weight, particularly preferably 0.1–5% by weight, in each case based on the total weight of the composition.

For use, the cosmetic and dermatological preparations according to the invention are applied to the skin and/or the hair in an adequate amount in the usual manner for cosmetics.

Cosmetic and dermatological preparations according to the invention may exist in various forms. Thus, they may be, for example, a solution, a water-free preparation, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous according to the invention are, for example, O/W emulsifiers, principally from the group consisting of the substances having HLB values of 11–16, very particularly advantageously having HLB values of 14.5–15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following:

polyethylene glycol (13)stearyl ether (steareth-13),
polyethylene glycol (14)stearyl ether (steareth-14),
polyethylene glycol (15)stearyl ether (steareth-15),
polyethylene glycol (16)stearyl ether (steareth-16),
polyethylene glycol (17)stearyl ether (steareth-17),
polyethylene glycol (18)stearyl ether (steareth-18),
polyethylene glycol (19)stearyl ether (steareth-19),
polyethylene glycol (20)stearyl ether (steareth-20),
polyethylene glycol (12)isostearyl ether (isosteareth-12),
polyethylene glycol (13)isostearyl ether (isosteareth-13),
polyethylene glycol (14)isostearyl ether (isosteareth-14),
polyethylene glycol (15)isostearyl ether (isosteareth-15),
polyethylene glycol (16)isostearyl ether (isosteareth-16),
polyethylene glycol (17)isostearyl ether (isosteareth-17),
polyethylene glycol (18)isostearyl ether (isosteareth-18),
polyethylene glycol (19)isostearyl ether (isosteareth-19),
polyethylene glycol (20)isostearyl ether (isosteareth-20),
polyethylene glycol (13)cetyl ether (ceteth-13),
polyethylene glycol (14)cetyl ether (ceteth-14),
polyethylene glycol (15)cetyl ether (ceteth-15),
polyethylene glycol (16)cetyl ether (ceteth-16),
polyethylene glycol (17)cetyl ether (ceteth-17),
polyethylene glycol (18)cetyl ether (ceteth-18),
polyethylene glycol (19)cetyl ether (ceteth-19),
polyethylene glycol (20)cetyl ether (ceteth-20),
polyethylene glycol (13)isocetyl ether (isoceteth-13),
polyethylene glycol (14)isocetyl ether (isoceteth-14),
polyethylene glycol (15)isocetyl ether (isoceteth-15),
polyethylene glycol (16)isocetyl ether (isoceteth-16),
polyethylene glycol (17)isocetyl ether (isoceteth-17),
polyethylene glycol (18)isocetyl ether (isoceteth-18),
polyethylene glycol (19)isocetyl ether (isoceteth-19),
polyethylene glycol (20)isocetyl ether (isoceteth-20),
polyethylene glycol (12)oleyl ether (oleth-12),
polyethylene glycol (13)oleyl ether (oleth-13),
polyethylene glycol (14)oleyl ether (oleth-14),
polyethylene glycol (15)oleyl ether (oleth-15),
polyethylene glycol (12)lauryl ether (laureth-12),
polyethylene glycol (12)isolauryl ether (isolaureth-12),
polyethylene glycol (13)cetylstearyl ether (ceteareth-13),
polyethylene glycol (14)cetylstearyl ether (ceteareth-14),
polyethylene glycol (15)cetylstearyl ether (ceteareth-15),
polyethylene glycol (16)cetylstearyl ether (ceteareth-16),
polyethylene glycol (17)cetylstearyl ether (ceteareth-17),
polyethylene glycol (18)cetylstearyl ether (ceteareth-18),
polyethylene glycol (19)cetylstearyl ether (ceteareth-19),
polyethylene glycol (20)cetylstearyl ether (ceteareth-20).

It is furthermore advantageous to select the fatty acid ethoxylates from the following group:

polyethylene glycol (20)stearate, polyethylene glycol (21) stearate, polyethylene glycol (22)stearate, polyethylene glycol (23)stearate, polyethylene glycol (24)stearate, polyethylene glycol (25)stearate, polyethylene glycol (12) isostearate, polyethylene glycol (13)isostearate, polyethylene glycol (14)isostearate, polyethylene glycol (15) isostearate, polyethylene glycol (16)isostearate, polyethylene glycol (17)isostearate, polyethylene glycol (18)isostearate, polyethylene glycol (19)isostearate, polyethylene glycol (20)isostearate, polyethylene glycol (21) isostearate, polyethylene glycol (22)isostearate, polyethylene glycol (23)isostearate, polyethylene glycol (24) isostearate, polyethylene glycol (25)isostearate, polyethylene glycol (12)oleate, polyethylene glycol (13) oleate, polyethylene glycol (14) oleate, polyethylene glycol (15)oleate, polyethylene glycol (16)oleate, polyethylene glycol (17)oleate, polyethylene glycol (18)oleate, polyethylene glycol (19)oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30)cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21)glyceryl laurate, polyethylene glycol (22)glyceryl laurate, polyethylene glycol (23)glyceryl laurate, polyethylene glycol (6)glyceryl caprate/caprinate, polyethylene glycol (20) glyceryl oleate, polyethylene glycol (20)glyceryl isostearate, polyethylene glycol (18)glyceryl oleate/cocoate.

It is likewise favourable to select the sorbitan esters from the group consisting of polyethylene glycol (20)sorbitan monolaurate, polyethylene glycol (20)sorbitan monostearate, polyethylene glycol (20)sorbitan monoisostearate, polyethylene glycol (20)sorbitan monopalmitate, polyethylene glycol (20)sorbitan monooleate.

Optional W/O emulsifiers, but ones which may nevertheless be advantageous for the purposes of the invention are the following:
fatty alcohols having from 8 to 30 carbon atoms, monoglycerol esters of saturated and/or unsaturated, branched and/or unbranched alkanecarboxylic acids having a chain length of from 8 to 24 carbon atoms, in particular 12–18 carbon atoms, diglycerol esters of saturated and/or unsaturated, branched and/or unbranched alkanecarboxylic acids having a chain length of from 8 to 24 carbon atoms, in particular 12–18 carbon atoms, monoglycerol ethers of saturated and/or unsaturated, branched and/or unbranched alcohols having a chain length of from 8 to 24 carbon atoms, in particular 12–18 carbon atoms, diglycerol ethers of saturated and/or unsaturated, branched and/or unbranched alcohols having a chain length of from 8 to 24 carbon atoms, in particular 12–18 carbon atoms, propylene glycol esters of saturated and/or unsaturated, branched and/or unbranched alkanecarboxylic acids having a chain length of from 8 to 24 carbon atoms, in particular 12–18 carbon atoms, and sorbitan esters of saturated and/or unsaturated, branched and/or unbranched alkanecarboxylic acids having a chain length of from 8 to 24 carbon atoms, in particular 12–18 carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

The preparation according to the invention is particularly suitable for protecting human skin against ageing processes and against oxidative stress, i.e. against damage caused by free radicals, as are produced, for example, by solar irradiation, heat or other influences. In this connection, it is in the various administration forms usually used for this application. For example, it may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The formulation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The cosmetic preparation according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes, are usually used.

The cosmetic formulation may also be used to protect the hair against photochemical damage in order to prevent colour changes, bleaching or damage of a mechanical nature. In this case, a suitable formulation is in the form of a rinse-out shampoo, lotion, gel or emulsion, the formulation in question being applied before or after shampooing, before or after colouring or bleaching or before or after permanent waving. It is also possible to select a formulation in the form of a lotion or gel for styling or treating the hair, in the form of a lotion or gel for brushing or blow-waving, in the form of a hair lacquer, permanent waving composition, colorant or bleach for the hair. Apart from the compound of the formula I, the cosmetic or pharmaceutical formulation may comprise various adjuvants used in this type of composition, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The cosmetic preparations according to the invention can be prepared using techniques which are well known to the person skilled in the art.

To protect the skin and/or natural or sensitised hair against sunlight, a cosmetic preparation comprising one or more compounds of the formula I is applied to the skin or the hair. Sensitised hair here is taken to mean hair which has been subjected to a chemical treatment, such as a permanent waving treatment, a colouring process or bleaching process.

Furthermore, it has also been noted that compounds of the formula I can have a stabilising effect on the formulation. When used in corresponding products, the latter are thus also stable for longer and do not change their appearance. In particular, the effectiveness of the ingredients, for example vitamins, is retained even in the case of application over extended periods or extended storage. This is particularly advantageous in the case of compositions for protecting the skin against the effect of UV rays since these cosmetics are exposed to particularly high stresses by UV radiation. In a 2,2-diphenyl-1-picrylhydrazyl (DPPH) assay, it was found that 4,6,3',4'-tetrahydroxybenzylcoumaranone has better free-radical scavenger properties than tocopherol (vitamin E). The performance of the DPPH assay is described in Brand-Williams, W., Cuvelier, M. E. & Berset, C. "Use of a free radical method to evaluate antioxidant activity"; *Food Science & Technology* 28, 25–30 (1995). Gamez, E. J. et al. "Antioxidant flavonoid glycosides from Daphniphyllum calycinum"; *J. Nat. Prod.* 61, 706–708 (1998); Ancerewicz, J. et al. "Structure-property relationships of trimetazidine derivatives and model compounds as potential antioxidants"; *Free Radic. Biol. Med.* 25, 113–120 (1998).

2,2-Diphenyl-1-picrylhydrazyl is a free radical which is stable in solution. The unpaired electron results in a strong absorption band at 515 nm, and the solution has a dark violet colour. In the presence of a free-radical scavenger, the electron is paired, the absorption disappears, and the decoloration proceeds stoichiometrically taking into account the electrons taken up. The absorbance is measured in a photometer. The anti-free-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which can be considered to be a property of the substance under the given measurement conditions. The substance investigated is compared with a standard (for example tocopherol).

The evaluation is carried out graphically by plotting the test substance/-DPPH molar ratio against the percentage decrease in absorbance, and the $EC_{50}$ is determined by reading off at 50%. In addition, the slope of the straight lines in the linear region is determined and the $EC_{50}$ calculated.

The positive effects of compounds of the formula I give rise to their particular suitability for use in cosmetic or pharmaceutical formulations.

The properties of compounds of the formula I should likewise be regarded as positive for use in foods or as food supplements or as functional foods. The further explanations given for foods also apply correspondingly to food supplements and functional foods.

The foods which can be enriched with one or more compounds of the formula I in accordance with the present invention include all materials which are suitable for consumption by animals or consumption by humans, for example vitamins and provitamins thereof, fats, minerals or amino acids. (The foods may be solid, but also liquid, i.e. in the form of a beverage). Foods which can be enriched with one or more compounds of the formula I in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I in accordance with the present invention are corn or cereals from a single plant species and materials produced from plant species of this type, such as, for example, cereal syrup, rye flour, wheat flour or oatbran. Mixtures of foods of this type are also suitable for being enriched with one or more compounds of the formula I in accordance with the present invention, for example multivitamin preparations, mineral mixtures or sweetened juice. As further examples of foods which can be enriched with one or more compounds of the formula I in accordance with the present invention, mention may be made of food preparations, for example prepared cereals, biscuits, mixed drinks, foods prepared especially for children, such as yoghurt, diet foods, low-calorie foods or animal feeds.

The foods which can be enriched with one or more compounds of the formula I in accordance with the present invention thus include all edible combinations of carbohydrates, lipids, proteins, inorganic elements, trace elements, vitamins, water or active metabolites of plants and animals.

The foods which can be enriched with one or more compounds of the formula I in accordance with the present invention are preferably administered orally, for example in the form of meals, pills, tablets, capsules, powders, syrup, solutions or suspensions.

The foods according to the invention enriched with one or more compounds of the formula I can be prepared using techniques which are well known to the person skilled in the art.

Due to their action as antioxidants or free-radical scavengers, compounds of the formula I containing radicals as defined above, where —X— is a single bond, —CH$_2$—, —C(O)—, =C(OR$^5$)—, —C(NR$^5$)—, —CH(NR$^5$R$^6$)— or —CH(OR$^5$)—, are also suitable as medicaments. In this case, they support or replace natural mechanisms which scavenge free radicals in the body. The compounds of the formula I can in some cases be compared in terms of their action with free-radical scavengers such as vitamin C. Compounds of the formula I can be used, for example, for preventative treatment of inflammation and allergies of the skin and in certain cases for preventing certain types of cancer.

Compounds of the formula I in which —X— is =CH— and at least one radical from R$^1$, R$^2$, R$^3$ and R$^4$ is a group selected from the following list:

straight-chain or branched C$_1$- to C$_{12}$-alkylcarbonyl groups,
straight-chain or branched C$_3$- to C$_{12}$-alkenylcarbonyl groups,
straight-chain or branched C$_1$- to C$_{12}$-hydroxyalkyl groups, in which the hydroxyl group may be bonded to a primary or secondary carbon atom of the chain, and furthermore the alkyl chain may also be interrupted by oxygen,
C$_3$- to C$_{10}$-cycloalkylcarbonyl groups and C$_3$- to C$_{12}$-cycloalkenyl and/or cycloalkenylcarbonyl groups, in which each of the rings may also be bridged by —(CH$_2$)$_n$— groups, where n=from 1 to 3,
aryl and/or arylcarbonyl groups,
heteroaryl and/or heteroarylcarbonyl groups, where these groups may be substituted by alkyl, hydroxyl, alkoxy, amino, mono- and di-alkylamino, sulfonic acid, carboxyl and/or halogen groups,
mono- and/or oligoglycosyl radicals,

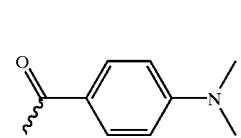
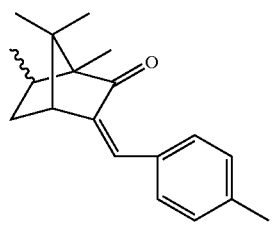

-continued

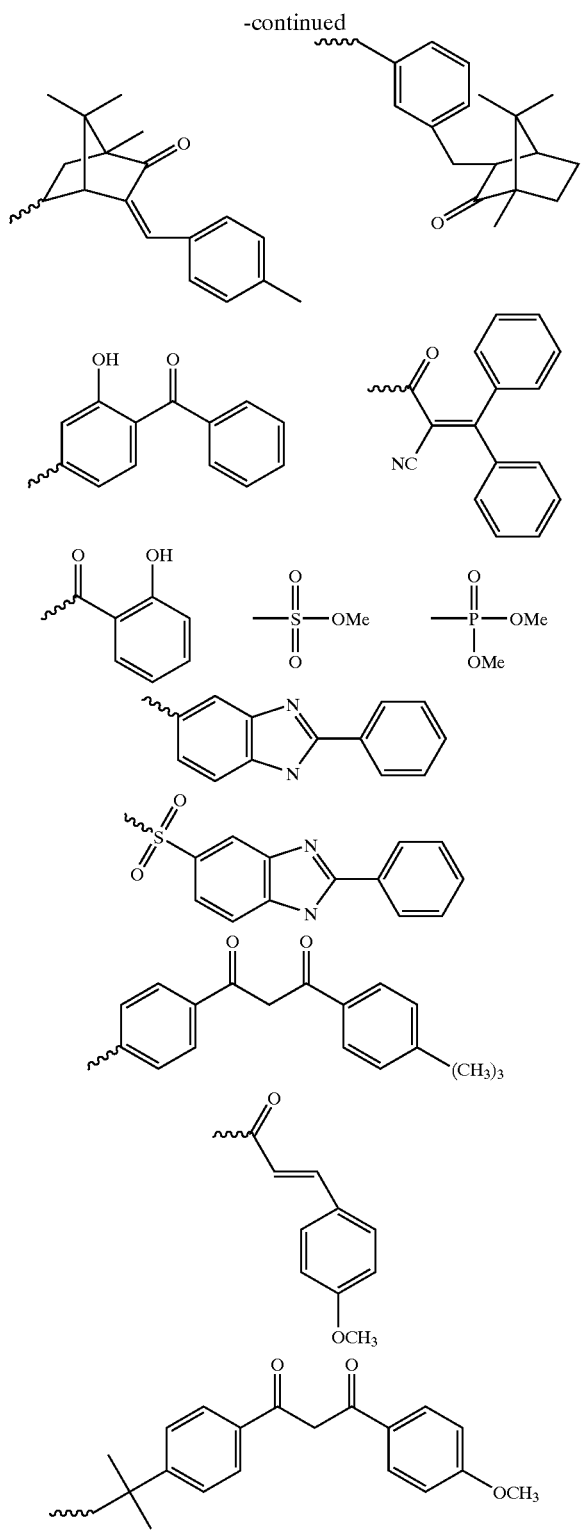
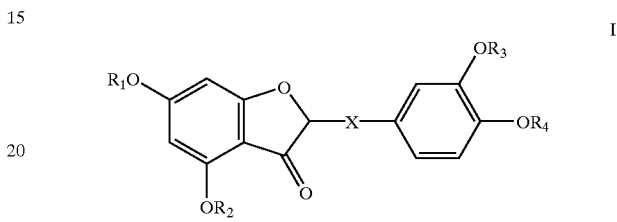

in which Me is a proton or an alkali metal ion, in particular a sodium or potassium ion, are also suitable as medicaments owing to the above-mentioned properties.

Compounds of the formula I are particularly suitable for the preparation of a medicament for the treatment of inflammation, allergies and irritation, in particular of the skin.

It is furthermore possible to prepare medicaments which act as a vein tonic, as an agent for increasing the strength of blood capillaries, as cuperose inhibitor, as chemical, physical or actinic erythema inhibitor, as agent for the treatment of sensitive skin, as decongestant, as desiccant, as slimming agent, as anti-wrinkle agent, as stimulator for the synthesis of components of the extracellular matrix, as strengthening agent for improving skin elasticity, and as anti-ageing agent.

Furthermore, compounds of the formula I exhibit antiallergic and anti-inflammatory and antiirritative actions. They are therefore suitable for the preparation of medicaments for the treatment of inflammation or allergic reactions.

The invention furthermore relates to compounds of the formula I $$R_1O\!-\!\!\overset{}{\underset{OR_2}{\diagup\!\!\!\diagdown}}\!\!-\!\!\overset{O}{\underset{O}{\diagup\!\!\!\diagdown}}\!\!-\!\!X\!-\!\!\overset{OR_3}{\diagup\!\!\!\diagdown}\!\!-\!\!OR_4 \qquad I$$

in which the variables are as defined above, which are characterised in that at least one radical from $R^1$, $R^2$, $R^3$ and $R^4$ is not H.

Through the radicals $R^1$, $R^2$, $R^3$ and $R^4$, the properties of the compounds can be matched virtually as desired to the respective needs. Thus, the introduction of, for example, alkyl chains enables the solubility of the compounds in oils to be improved. The introduction of UV-absorbent groups enables the preparation of compounds which are both antioxidants or free-radical scavengers and UV absorbers. The radicals can be introduced, for example, starting from the known compounds 4,6,3',4'-tetra-hydroxybenzylcoumaran-3-one (X=—CH$_2$—) or 4,6,3',4'-tetrahydroxyaurone (X=CH—) by processes known per se to the person skilled in the art. Thus, alkyl chains can be introduced by reaction of the parent compounds with the corresponding alkyl halides in the presence of a strong base in a suitable solvent, for example dimethylformamide. If the radicals $R^1$ to $R^4$ form an ester bond, this can be carried out, for example, by reaction with a corresponding acid chloride. General preparation processes are described, for example, in Houben-Weyl; Georg Thieme Verlag, Stuttgart. Some suitable reactions are mentioned below as representative:

Linking by ester formation: Houben-Weyl; Volume VIII, pp. 503 ff.; editor: E. Müller, Houben-Weyl; Volume E5, pp. 656 ff.; editor: J. Falbe. Linking by ether formation: Houben-Weyl; Volume VI/3, pp. 1 ff.; editor: E. Müller.

Linking by sulfonic acid ester: Houben-Weyl; Volume IX; pp. 659 ff.; editor: E. Müller.

Some precursors of the radicals R which are suitable for introduction of the radicals into the parent compounds are indicated in scheme 1 as representative. This list is only illustrative and shows only a small selection from the range of possible precursors. It is readily possible for the person skilled in the art to provide other suitable leaving groups, for example a tosylate group or a triflate group, instead of the halides. For example, introduction of the radicals via an ester function is also possible through corresponding transesterification reactions.

Scheme 1: Examples of suitable precursors for the introduction of radicals $R^1$, $R^2$, $R^3$, $R^4$:

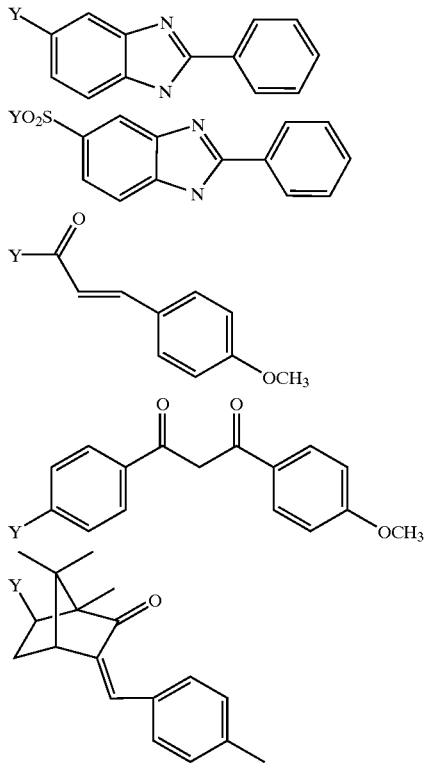

Y here is a suitable leaving group.

The compounds may either be in the form of pure compounds, i.e., for example, only certain radicals are formed by the groups indicated above, while the other radicals are hydrogen. However, it is also possible for the radicals to be randomly distributed, i.e., for example, in the form of an isomer mixture or a mixture of compounds in which 1, 2, 3 or 4 hydrogen atoms of the parent compound have been replaced by one or more of the radicals indicated above.

The preferred compounds according to the invention include the compounds in which at least one radical from $R^1$, $R^2$, $R^3$ and $R^4$ is an —SO₃Me or —PO₃Me₂ group. These compounds have improved water solubility compared with the hydroxyl compounds and can therefore be incorporated readily into water-containing formulations. Particular preference is given here to the sulfates, in particular the trisulfates of the formula III

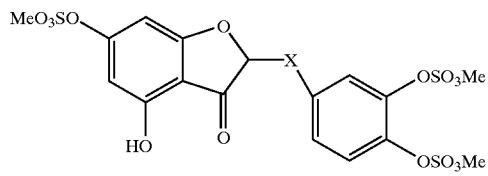

III which may be in pure form or in the form of a mixture with the corresponding mono- and disulfates. Particular preference is given to the sulfate, in particular the trisulfate, of 4,6,3',4'-tetrahydroxybenzylcoumaran-3-one

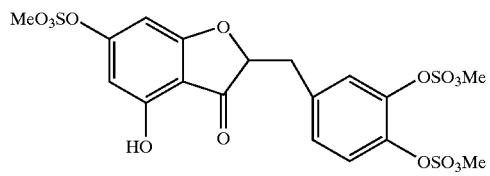

which is preferably employed in the form of a soluble salt, preferably an alkali metal salt, and is either in pure form, or, in a further preferred embodiment, in the form of a mixture with the mono- and disulfate.

For the purposes of the invention, particular preference is given to compounds of the formula I in which —X— is a single bond, —CH₂—, —C(O)—, =C(OR⁵)—, —C(NR⁵)—, —CH(NR⁵R⁶)— or —CH(OR⁵)—.

A reaction of the parent compound with the corresponding reactive precursors of the radicals $R^1$ to $R^4$ is carried out by processes known to the person skilled in the art and in the usual solvents. Suitable solvents are, for example, chlorinated hydrocarbons, dimethyl sulfoxide, dimethylformamide, etc.

The present invention furthermore relates to the use of a preferred compound of the formula I according to the invention in which —X— is a single bond, —CH₂—, —C(O)—, =C(OR⁵)—, —C(NR⁵)—, —CH(NR⁵R⁶)— or —CH(OR⁵)—, and the other variables have the general meaning given above, as an antioxidant, in particular for cosmetic formulations or foods.

The invention furthermore relates to the stabilisation of UV filters. A known and effective class of light-protection filter substances is formed by dibenzoylmethane derivatives. However, it is disadvantageous that these substances are very easily decomposed by UV light, and their protective properties are thus lost. An example of a light-protection filter from this class of compounds which is available on the market is 4-(tert-butyl)-4'-methoxydibenzoylmethane, which has the following structure:

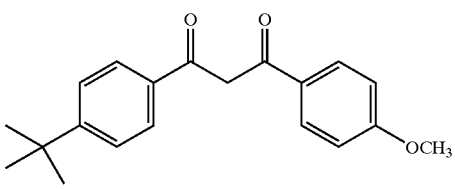

Surprisingly, it has now been found that compounds of the formula I in which —X— is a single bond, —CH₂—, —C(O)—, =C(OR⁵)—, —C(NR⁵)—, —CH(NR⁵R⁶)— or —CH(OR⁵)— have a very good stabilisation action for dibenzoylmethanes, in particular 4-(tert-butyl)-4-methoxybenzoylmethane. A particularly high stabilisation action has been found for a compound of the formula I in which X =—CH₂— and $R^1=R^2=R^3=R^4=H$. By incorporating mixtures of these compounds into cosmetics, it is now possible to prepare light stabilisers using dibenzoylmethanes which exhibit only a slight reduction in the protective action against UV rays, or none at all, even on extended exposure to the sun, for example during sunbathing for a number of hours.

The invention is explained in greater detail by means of examples and with reference to a drawing.

In the formulations listed below, "sulfated coumaranone, potassium salt" or THBC sulfate is taken to mean a mixture of the mono-, di- and trisulfates of 4,6,3',4'- tetrahydroxybenzylcoumaran-3-one in which the compounds in the mixture are in the form of the potassium salt.

Antaron® V-220 is marketed by GAF, Frechen, Del.

Carbomer Ultrez-10 is sold by Goodrich, Neuss, Del.

Dehymuls® E is a mixture of dicocoyl pentaerythrityl citrate, sorbitol sesquioleate, beeswax and aluminium stearate and is marketed by Henkel KGaA, Düsseldorf, DE.

Eusolex® 2292, Eusolex® HMS, Eusolex® 6300 and Eusolex® 232 are UV filters which are marketed by Merck KGaA, Darmstadt.

HMLO stands for 5-hydroxy-5-methyllaurophenone oxime.

Luvitol® EHO is marketed by BASF AG, Ludwigshafen, DE.

MBTTBP is 2,2'-methylenebis(6-2H-benzotriazol-2-yl)-4-(1,1,3,3-tetramethylbutyl)phenol.

Pemulen® TR-1 is an acrylate/$C_{10}$–$C_{30}$-alkyl acrylate polymer which is marketed by Goodrich, Neuss, DE.

Pemulen® TR-2 is an acrylate/$C_{10}$–$C_{30}$-alkyl acrylate polymer which is marketed by Goodrich, Neuss.

Performa® V825 is a synthetic wax which is marketed by New Phase, N.J.08554.

Oxynex® K is a mixture of PEG-8, tocopherol, ascorbyl palmitate, ascorbic acid and citric acid and is marketed by Merck KGaA, Darmstadt.

Uvasorb® HEB is a dioctylbutamidotriazone and is marketed by 3V Sigma.

EXAMPLE 1

| | Care lotion (W/O) for application to the skin | % by wt. |
|---|---|---|
| A | 4,6,3',4'-Tetrahydroxybenzylcoumaran-3-one | 1.00 |
| | Polyglyceryl 2-dipolyhydroxystearate | 5.00 |
| | Beeswax | 0.50 |
| | Zinc stearate | 0.50 |
| | Hexyl laurate | 9.00 |
| | Cetyl isononanoate | 6.00 |
| | Shea butter | 0.50 |
| | DL-α-Tocopherol acetate | 1.00 |
| B | Glycerol | 5.00 |
| | Magnesium sulfate heptahydrate | 1.00 |
| | Preservatives | q.s. |
| | Water, demineralised | aqua to 100.00 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The preservatives used are the following:
0.05% of propyl 4-hydroxybenzoate
0.15% of methyl 4-hydroxybenzoate

EXAMPLE 2

| | Care lotion (W/O) for application to the skin | % by wt. |
|---|---|---|
| A | Polyglyceryl 2-dipolyhydroxystearate | 5.00 |
| | Beeswax | 0.50 |
| | Zinc stearate | 0.50 |
| | Hexyl laurate | 9.00 |
| | Cetyl isononanoate | 6.00 |
| | Shea butter | 0.50 |
| | DL-α-Tocopherol acetate | 1.00 |
| B | Sulfated coumaranone, potassium salt | 0.50 |
| | Glycerol | 5.00 |

| Care lotion (W/O) for application to the skin | % by wt. |
|---|---|
| Magnesium sulfate heptahydrate | 1.00 |
| Preservative | q.s. |
| Water, demineralised | to 100.00 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The preservatives used are the following:
0.05% of propyl 4-hydroxybenzoate
0.15% of methyl 4-hydroxybenzoate

EXAMPLE 3

| | Skin cream (O/W) | % by wt. |
|---|---|---|
| A | Paraffin | 2.00 |
| | Isohexadecane | 2.00 |
| | Isopropyl palmitate | 3.00 |
| | Soya oil | 0.50 |
| | Dimethicone | 1.00 |
| | Cetyl alcohol | 1.00 |
| | Sorbitol stearate | 1.50 |
| | Cetyl alcohol (and) cetyl glycoside | 4.00 |
| | (-)-α-Bisabolol | 0.30 |
| B | Water, demineralised | to 100.00 |
| | Sulfated coumaranone, potassium salt | 0.20 |
| | Glycerol, 87% | 10.00 |
| | D-Panthenol | 0.50 |
| | D-(+)-Biotin | 0.05 |
| | Preservatives | q.s. |
| C | Xanthan gum | 0.30 |
| D | Perfume | 0.20 |

Preparation

Phase A and phase B are warmed separately to 75° C. Phase C is then slowly added to phase B and stirred until the mixture is homogenised. The resultant mixture B/C is added to phase A at a temperature of 75° C., and the mixture is homogenised. After cooling to 35° C., perfumes are added.

The preservatives used are 0.05% of propyl 4-hydroxybenzoate, 0.15% of methyl 4-hydroxybenzoate and 0.30% of Germall 115 (ISP, Frechen).

EXAMPLE 4

| | | % by wt. |
|---|---|---|
| A | 4,6,3',4'-Tetrahydroxybenzylcoumaran-3-one | 0.10 |
| | Paraffin | 2.00 |
| | Isohexadecane | 2.00 |
| | Isopropyl palmitate | 3.00 |
| | Soya oil | 0.50 |
| | Dimethicone | 1.00 |
| | Cetyl alcohol | 1.00 |
| | Sorbitol stearate | 1.50 |
| | Cetyl alcohol (and) cetyl glycoside | 4.00 |
| | (-)-α-Bisabolol | 0.30 |
| B | Water, demineralised | to 100.00 |
| | Glycerol, 87% | 10.00 |
| | D-Panthenol | 0.50 |
| | D-(+)-Biotin | 0.05 |
| | Preservatives | q.s. |
| C | Xanthan gum | 0.30 |
| D | Perfume | 0.20 |

Preparation

Phase A and phase B are warmed separately to 75° C. Phase C is then slowly added to phase B and stirred until the mixture is homogenised. The resultant mixture B/C is added to phase A at a temperature of 75° C., and the mixture is homogenised. After cooling to 35° C., perfumes are added.

The preservatives used are the following:
0.05% of propyl 4-hydroxybenzoate
0.15% of methyl 4-hydroxybenzoate
0.30% of Germall 115 (ISP, Frechen).

EXAMPLE 5

|   | Sunscreen spray (O/W) | % by wt. |
|---|---|---|
| A | 4,6,3',4'-Tetrahydroxybenzylcoumaran-3-one | 0.50 |
|   | Eusolex ® 2292 (Art. No. 105382) | 7.50 |
|   | Eusolex ® HMS (Art. No. 111412) | 7.00 |
|   | Steareth-2 | 0.40 |
|   | Steareth-10 | 0.80 |
|   | Pemulen ® TR-2 | 0.18 |
|   | Propylene glycol isoceteth-3 acetate | 5.00 |
|   | Performa ® V 825 | 0.80 |
|   | Dimethicone | 1.00 |
|   | Oxynex ® K (Art. No. 108324) | 0.10 |
| B | Eusolex ® 232 (Art. No. 105372) | 1.00 |
|   | Triethanolamine | 0.90 |
|   | Propane-1,2-diol | 2.00 |
|   | Preservative | 0.50 |
|   | Water, demineralised | to 100.00 |

Preparation

Phase B

The water is mixed with the triethanolamine, and Eusolex® 232 is subsequently added with stirring. As soon as everything has dissolved, the further constituents of phase B are added and the mixture is subsequently warmed to 80° C.

Phase A

The constituents of phase A with the exception of Pemulen® TR-2 are combined and warmed to 80° C. The Pemulen® TR-2 is subsequently added with stirring.

Preparation of the Sunscreen

Phase B is slowly added to phase A with stirring. After homogenisation, the mixture is cooled with stirring.

The preservatives used are the following:
0.05% of propyl 4-hydroxybenzoate
0.15% of methyl 4-hydroxybenzoate

EXAMPLE 6

|   | Sunscreen spray (01W) | % by wt. |
|---|---|---|
| A | Eusolex ® 2292 (Art. No. 105382) | 7.50 |
|   | Eusolex ® HMS (Art. No. 111412) | 7.00 |
|   | Steareth-2 | 0.40 |
|   | Steareth-10 | 0.80 |
|   | Pemulen ® TR-2 | 0.18 |
|   | Propylene glycol isoceteth-3 acetate | 5.00 |
|   | Performa ® V 825 | 0.80 |
|   | Dimethicone | 1.00 |
|   | Oxynex ® K (Art. No. 108324) | 0.10 |
| B | Sulfated coumaranone, potassium salt | 0.20 |
|   | Eusolex ® 232 (Art. No. 105372) | 1.00 |
|   | Triethanolamine | 0.90 |
|   | Propane-1,2-diol | 2.00 |
|   | Water, demineralised | aqua to 100.00 |

Preparation

Phase B

The water is mixed with the triethanolamine, and Eusolex® 232 is subsequently added with stirring. As soon as everything has dissolved, the further constituents of phase B are added and the mixture is subsequently warmed to 80° C.

Phase A

The constituents of phase A with the exception of Pemulen® TR-2 are combined and warmed to 80° C. The Pemulen® TR-2 is subsequently added with stirring.

Preparation of the Sunscreen

Phase B is slowly added to phase A with stirring. After homogenisation, the mixture is cooled with stirring.

The preservatives used are the following:
0.05% of propyl 4-hydroxybenzoate
0.15% of methyl 4-hydroxybenzoate

EXAMPLE 7

|   | Sunscreen gel (aqueous) | % by wt. |
|---|---|---|
| A | 4,6,3',4'-Tetrahydroxybenzylcoumaran-3-one | 0.10 |
|   | Eusolex ® 232 (Art. No. 105372) | 4.00 |
|   | Sodium hydroxide solution | 6.00 |
|   | Glycerol | 3.00 |
|   | Propane-1,2-diol | 2.00 |
|   | Preservatives | q.s. |
|   | Water, demineralised | to 100.00 |
| B | Carbomer Ultrez-10 | 0.70 |
|   | Water, demineralised | 60.00 |
| C | Sodium hydroxide solution (10%) | 1.50 |
|   | Water, demineralised | 4.00 |

Preparation

Carbomer Ultrez-10 is completely dispersed in the water of phase B. Phase C is subsequently added slowly, and the mixture is homogenised. For phase A, firstly the water is added to the sodium hydroxide solution and then the Eusolex® 232 is added and completely dissolved with stirring. When a clear solution has been obtained, the further constituents of phase A are added. Phase A is subsequently added in portions to the mixture of phases B and C, with homogenisation after each addition.

The preservative used is the following:
0.20% of methyl 4-hydroxybenzoate

EXAMPLE 8

|   | Sunscreen gel (O/W) | % by wt. |
|---|---|---|
| A | 4,6,3',4'-Tetrahydroxybenzylcoumaran-3-one | 0.10 |
|   | Eusolex ® 6300 (Art. No. 5385) | 0.75 |
|   | Luvitol ® EHO | 10.00 |
|   | Dimethicone | 2.00 |
|   | Shea butter | 5.00 |
|   | Antaron ® V-220 | 2.00 |
|   | Oxynex ® K | 1.00 |
| B | Eusolex ® 232 (Art. No. 5372) | 0.75 |
|   | Tris(hydroxymethyl)aminomethane | 0.33 |
|   | Preservatives | q.s. |
|   | Water, demineralised | 20.00 |
| C | Tris(hydroxymethyl)aminomethane | 1.20 |
|   | Water, demineralised | 10.00 |
| D | Pemulen ® TR-1 | 0.60 |
|   | Water, demineralised | to 100.00 |

Preparation

The Pemulen® TR-1 is dissolved in the water of phase D. The tris(hydroxymethyl)aminomethane is dissolved in the water of phase C, and the solution is added to phase D. The tris(hydroxymethyl)aminomethane is dissolved in the water of phase B, and the Eusolex® 232 is then added with stirring. When a clear solution has been obtained, the further constituents of phase B are added, and phase B is then added to the mixture of phases C and D, and the mixture is homogenised. The constituents of phase A are combined and warmed. Phase A is then added to the mixture of the remaining phases with homogenisation.

The preservatives used are the following:
0.05% of propyl 4-hydroxybenzoate
0.15% of methyl 4-hydroxybenzoate

EXAMPLE 9

| | Sunscreen gel (O/W) | % by wt. |
|---|---|---|
| A | Eusolex ® 6300 (Art. No. 5385) | 0.75 |
| | Luvitol ® EHO | 10.00 |
| | Dimethicone | 2.00 |
| | Shea butter | 5.00 |
| | Antaron ® V-220 | 2.00 |
| | Oxynex ® K liquid (Arty. No. 8324) | 1.00 |
| B | Sulfated coumaranone, potassium salt | 1.00 |
| | Eusolex ® 232 (Art. No. 5372) | 0.75 |
| | Tris(hydroxymethyl)aminomethane | 0.33 |
| | Preservatives | q.s. |
| | Water, demineralised | 20.00 |
| C | Tris(hydroxymethyl)aminomethane | 1.20 |
| | Water, demineralised | 10.00 |
| D | Pemulen ® TR-1 | 0.60 |
| | Water, demineralised | to 100.00 |

Preparation

The Pemulen® TR-1 is dissolved in the water of phase D. The tris(hydroxymethyl)aminomethane is dissolved in the water of phase C, and the solution is added to phase D. The tris(hydroxymethyl)aminomethane is dissolved in the water of phase B, and the Eusolex® 232 is then added with stirring. When a clear solution has been obtained, the further constituents of phase B are added, and phase B is then added to the mixture of phases C and D, and the mixture is homogenised. The constituents of phase A are combined and warmed. Phase A is then added to the mixture of the remaining phases with homogenisation.

The preservatives used are the following: 0.05% of propyl 4-hydroxybenzoate and 0.15% of methyl 4-hydroxybenzoate.

EXAMPLE 10

| | Sunscreen lotion (W/O) with UVA/B protection | % by wt. |
|---|---|---|
| A | 4,6,3',4'-Tetrahydroxybenzylcoumaran-3-one | 0.05 |
| | Eusolex ® 2292 (Art. No. 1.05382) | 3.00 |
| | Eusolex ® 4360 (Art. No. 1.05376) | 2.00 |
| | Dehymuls ® E | 6.00 |
| | Hardened castor oil | 1.00 |
| | Beeswax | 2.00 |
| | Oleyl erucate | 6.00 |
| | Decyl oleate | 6.00 |
| | Dicapryl ether | 5.00 |
| | Dimethicone | 1.00 |
| B | Glycerol (87%) | 5.00 |
| | Magnesium sulfate heptahydrate | 1.00 |
| | Preservatives | q.s. |
| | Water, demineralised | to 100.00 |

Preparation

The constituents of phases A and B are combined separately. Phase A is warmed to 75° C. and phase B separately to 80° C. Phase B is added to phase A with homogenisation. The mixture is subsequently cooled with stirring.

The preservatives used are the following:
0.05% of propyl 4-hydroxybenzoate
0.15% of methyl 4-hydroxybenzoate

EXAMPLE 11

| | Sunscreen lotion (W/O) with UVA/B protection | % by wt. |
|---|---|---|
| A | Eusolex ® 2292 (Art. No. 1.05382) | 3.00 |
| | Eusolex ® 4360 (Art. No. 1.05376) | 2.00 |
| | Dehymuls ® E | 6.00 |
| | Hardened castor oil | 1.00 |
| | Beeswax | 2.00 |
| | Oleyl erucate | 6.00 |
| | Decyl oleate | 6.00 |
| | Dicapryl ether | 5.00 |
| | Dimethicone | 1.00 |
| B | Sulfated coumaranone, potassium salt | 0.50 |
| | Glycerol (87%) | 5.00 |
| | Magnesium sulfate heptahydrate | 1.00 |
| | Preservatives | q.s. |
| | Water, demineralised | to 100.00 |

Preparation

The constituents of phases A and B are combined separately. Phase A is warmed to 75° C. and phase B separately to 80° C. Phase B is added to phase A with homogenisation. The mixture is subsequently cooled with stirring.

The preservatives used are the following:
0.05% of propyl 4-hydroxybenzoate
0.15% of methyl 4-hydroxybenzoate

EXAMPLE 12

Preparation of 4,6,3',4'-tetrahydroxycoumaran-3-one 10 g of quercetin are introduced in portions into 1 l of boiling water. 85 g of sodium carbonate and 200 g of sodium dithionite are subsequently added, and the suspension is stirred at 100° C. for 25 minutes. The mixture is then cooled to 5° C., and 130 ml of fuming hydrochloric acid (37%) are slowly added dropwise. The mixture is stirred at low temperature for a further 2 hours and subsequently filtered. The 2.6 g residue consists of 4,6,3',4'-tetrahydroxycoumaranone which is still contaminated with quercetin.

The filtrate is extracted firstly with 700 ml and subsequently with 200 ml of ethyl acetate. The combined organic phases are washed with water (200 ml), saturated NaCl solution (200 ml) and dried over sodium sulfate. After filtration, the solvent is distilled off under reduced pressure, giving a yellow solid (4.53 g).

EXAMPLE 13

Preparation of Sulfated 4,6,3',4'-tetrahydroxybenzylcoumaran-3-one 23.8 g of tetrabutylammonium hydrogensulfate and 21.7 g of N,N'-dicyclohexylcarbodiimide were dissolved in 250 ml of dry pyridine. 10 g of 4,6,3',4'-tetrahydroxybenzylcoumaran-3-one were then added, and the mixture was stirred at 50° C. overnight. After cooling to room temperature, the mixture was filtered, and 250 ml of methanol were added to the filtrate. After the mixture had been left to stand overnight, the precipitate was again filtered off, the filtrate was evaporated to 150 ml under reduced pressure, and the precipitate was again filtered off. A solution of 1.5 g of potassium carbonate in 250 ml of methanol was added to the filtrate. After 5 ml of water had been added to the mixture, the mixture was transferred into two centrifuge tubes and centrifuged. The liquid phase was decanted off, and the solid residue was dried in a vacuum drying cabinet.

Yield: 2.23 g of pale-brown powder, mixture of tri-, di- and monosulfate.

EXAMPLE 14

Determination of the $EC_{50}$ of 4,6,3',4'-tetrahydroxybenzylcoumaranone by DPPH Assay A 70 µM stock solution of 2,2-diphenyl-1-picrylhydrazyl (DPPH) in ethanol was prepared. Such amounts of 4,6,3',4'-tetrahydroxybenzylcoumaranone (THBC) were added to aliquots of this solution so as to give the THBC/DPPH ratios indicated in Table 1. The absorbance was in each case measured at 515 nm, 25° C. and 1 cm, with Table 1 in each case indicating the value measured at constant absorbance. The values are plotted graphically against one another in FIG. 1, with the molar ratio being plotted on the x axis and the measured absorbance as a relative proportion of the absorbance measured for the stock solution (100%) being plotted on the y axis.

The $EC_{50}$ determined was 0.17. The concentration of test substance employed at the $EC_{50}$ value was 8.7 pmol.

Using the same experimental set-up, an $EC_{50}$ of 0.21 was determined for tocopherol. 4,6,3',4'-Tetrahydroxycoumaranone is thus a more potent antioxidant than tocopherol (vitamin E).

TABLE 1

Absorbance determination in the DPPH assay

| THBC/DPPH | Absorbance in %, based on absorbance without THBC |
|---|---|
| 0 | 100 |
| 0.01 | 97.66 |
| 0.02 | 94.04 |
| 0.05 | 87.02 |
| 0.07 | 79.15 |
| 0.10 | 72.13 |
| 0.12 | 62.72 |
| 0.18 | 44.18 |
| 0.24 | 26.08 |
| 0.30 | 16.16 |
| 0.37 | 15.73 |
| 0.43 | 15.27 |
| 0.49 | 15.27 |
| 0.55 | 15.27 |
| 0.61 | 15.05 |
| 0.73 | 14.19 |
| 0.97 | 14.56 |
| 1.21 | 14.56 |

EXAMPLE 15

| O/W emulsion | % by wt. |
|---|---|
| Stearic acid | 1.50 |
| Glyceryl stearate SE | 3.50 |
| Caprylic acid/capric acid triglyceride | 5.00 |
| Octyldodecanol | 5.00 |
| Dicapryl ether | 5.00 |
| Cetylstearyl alcohol | 0.50 |
| Xanthan gum | 0.50 |
| Octyltriazone | 0.50 |
| MBTTBP | 6.00 |
| Titanium dioxide | 2.00 |
| α-Glycosylrutin | 0.20 |
| Glycerol | 3.00 |
| Sodium hydroxide solution, 45% | 0.03 |
| THBC | 0.10 |
| Ectoin | 1.00 |
| Preservative | 0.50 |
| Water | to 100.00 |

EXAMPLE 16

| O/W emulsion | % by wt. |
|---|---|
| Stearic acid | 1.50 |
| Glyceryl stearate SE | 3.50 |
| Caprylic acid/capric acid triglyceride | 9.00 |
| Octyldodecanol | 9.00 |
| Dicaprylyl ether | 9.00 |
| Cetylstearyl alcohol | 0.50 |
| Xanthan gum | 0.50 |
| Dibenzoylmethane | 2.00 |
| Methylbenzylidenecamphor | 4.00 |
| Boron nitride | 0.50 |
| α-Glycosylrutin | 0.50 |
| Glycerol | 5.00 |
| Sodium hydroxide solution, 45% | 0.03 |
| THBC | 0.20 |
| HMLO | 0.30 |
| EDTA solution | 1.00 |
| Preservative | 0.50 |
| Water | to 100.00 |

EXAMPLE 17

| O/W emulsion | % by wt. |
|---|---|
| Sorbitan stearate | 2.00 |
| Polyglyceryl 3-methylglucose distearate | 4.00 |
| Caprylic acid/capric acid triglyceride | 5.00 |
| Octyldodecanol | 5.00 |
| Dicaprylyl ether | 5.00 |
| Xanthan gum | 0.50 |
| Octyltriazone | 2.00 |
| Uvasorb HEB | 8.00 |
| THBC | 0.35 |
| HMLO | 0.10 |
| Glycerol | 3.00 |
| Phenylbenzimidazolesulfonic acid | 2.00 |
| Sodium hydroxide solution, 45% | 0.70 |
| Ectoin | 2.00 |
| Preservative | 0.50 |
| Water | to 100.00 |

EXAMPLE 18

| O/W emulsion | % by wt. |
|---|---|
| Sorbitan stearate | 2.00 |
| Polyglyceryl 3-methylglucose distearate | 4.00 |
| Caprylic acid/capric acid triglyceride | 5.00 |
| Octyldodecanol | 5.00 |
| Dicaprylyl ether | 5.00 |
| Xanthan gum | 0.50 |
| Dibenzoylmethane | 2.00 |
| Methylbenzylidenecamphor | 4.00 |
| THBC sulfate | 0.20 |
| Boron nitride | 1.00 |
| Ectoin | 2.00 |

-continued

| O/W emulsion | % by wt. |
|---|---|
| Glycerol | 5.00 |
| Phenylbenzimidazolesulfonic acid | 1.00 |
| Sodium hydroxide solution, 45% | 0.35 |
| EDTA solution | 1.00 |
| Preservative | 0.50 |
| Water | to 100.00 |

EXAMPLE 19

| O/W emulsion | % by wt. |
|---|---|
| Butylene glycol dicaprylate/dicaproate | 10.00 |
| Shea butter | 0.50 |
| Phenyltrimethicone | 2.00 |
| Acrylate/$C_{10-30}$-alkyl acrylate crosspolymer | 0.50 |
| Xanthan gum | 0.50 |
| T 150 | 3.00 |
| α-Glycosylrutin | 1.20 |
| THBC sulfate | 0.30 |
| Ectoin | 0.10 |
| Glycerol | 3.00 |
| Citric acid | 0.40 |
| Sodium hydroxide solution, 45% | 0.15 |
| Preservative | 0.50 |
| Water | to 100.00 |

EXAMPLE 20

| Hydrodispersion | % by wt. |
|---|---|
| Butylene glycol dicaprylate/dicaproate | 10.00 |
| Shea butter | 0.50 |
| Phenyltrimethicone | 2.00 |
| Acrylate/$C_{10-30}$-alkyl acrylate crosspolymer | 0.50 |
| Xanthan gum | 0.50 |
| Dibenzoylmethane | 1.00 |
| Methylbenzylidenecamphor | 2.00 |
| Uvasorb HEB | 4.00 |
| THBC | 0.30 |
| 5-Hydroxyectoin | 1.00 |
| Glycerol | 3.00 |
| Citric acid | 0.40 |
| Sodium hydroxide solution, 45% | 0.15 |
| EDTA solution | 1.00 |
| Preservative | 0.50 |
| Water | to 100.00 |

EXAMPLE 21

| W/O emulsion | % by wt. |
|---|---|
| Glyceryl lanolate | 1.00 |
| Polyglyceryl 2-dipolyhydroxystearate | 4.00 |
| Mineral oil | 8.00 |
| Butylene glycol dicaprylated/dicaproate | 12.00 |
| Isohexadecane | 6.00 |
| Dibenzoylmethane | 1.00 |
| Methylbenzylidenecamphor | 2.00 |
| MBTTBP | 4.00 |
| THBC | 0.20 |
| Boron nitride | 2.00 |
| Titanium dioxide | 2.00 |
| Glycerol | 5.00 |

-continued

| W/O emulsion | % by wt. |
|---|---|
| Magnesium sulfate | 0.70 |
| EDTA solution | 1.00 |
| Preservative | 0.50 |
| Water | to 100.00 |

EXAMPLE 22

| W/O emulsion | % by wt. |
|---|---|
| Glyceryl lanolate | 1.00 |
| Polyglyceryl 2-dipolyhydroxystearate | 5.00 |
| Mineral oil | 8.00 |
| Butylene glycol dicaprylate/dicaproate | 12.00 |
| Isohexadecane | 6.00 |
| THBC | 0.50 |
| Glycerol | 3.00 |
| Magnesium sulfate | 0.70 |
| Preservative | 0.50 |
| Water | to 100.00 |

EXAMPLE 23

| W/O emulsion | % by wt. |
|---|---|
| PEG 30 dipolyhydroxystearate | 4.00 |
| Mineral oil | 9.00 |
| Butylene glycol dicaprylate/dicaproate | 9.00 |
| $C_{12-15}$-Alkyl benzoate | 9.00 |
| Dibenzoylmethane | 2.00 |
| Methylbenzylidenecamphor | 4.00 |
| MBTTBP | 4.00 |
| THBC sulfate | 0.50 |
| α-Glycosylrutin | 0.50 |
| Glycerol | 3.00 |
| Magnesium sulfate | 0.70 |
| EDTA solution | 1.00 |
| Preservative | 0.50 |
| Water | to 100.00 |

EXAMPLE 24

| W/O emulsion | % by wt. |
|---|---|
| PEG 30 dipolyhydroxystearate | 4.00 |
| Mineral oil | 9.00 |
| Butylene glycol dicaprylate/dicaproate | 9.00 |
| $C_{12-15}$-Alkyl benzoate | 9.00 |
| Ectoin | 0.10 |
| T 150 | 3.00 |
| Uvasorb HEB | 2.00 |
| Octocrylene | 10.00 |
| THBC | 0.05 |
| Boron nitride | 2.00 |
| Titanium dioxide | 2.00 |
| Glycerol | 3.00 |
| Magnesium sulfate | 0.70 |
| Preservative | 0.50 |
| Water | to 100.00 |

EXAMPLE 25

| W/O emulsion | % by wt. |
| --- | --- |
| Cetyldimethicone copolyol | 4.00 |
| Mineral oil | 9.00 |
| Butylene glycol dicaprylate/dicaproate | 9.00 |
| $C_{12-15}$-Alkyl benzoate | 9.00 |
| Dibenzoylmethane | 2.00 |
| Methylbenzylidenecamphor | 4.00 |
| 5-Hydroxyectoin | 5.00 |
| THBC | 0.20 |
| Glycerol | 5.00 |
| Magnesium sulfate | 0.70 |
| EDTA solution | 1.00 |
| Preservative | 0.50 |
| Water | to 100.00 |

EXAMPLE 26

| W/O emulsion | % by wt. |
| --- | --- |
| Cetyldimethicone copolyol | 3.00 |
| Mineral oil | 9.00 |
| Butylene glycol dicaprylate/dicaproate | 9.00 |
| $C_{12-15}$-Alkyl benzoate | 9.00 |
| Ectoin | 0.05 |
| THBC sulfate | 0.50 |
| Glycerol | 3.00 |
| Magnesium sulfate | 0.70 |
| EDTA solution | 1.00 |
| Preservative | 0.50 |
| Water | to 100.00 |

EXAMPLE 27

| O/W emulsion | % by wt. |
| --- | --- |
| Stearic acid | 1.50 |
| Glycerol monostearate | 3.00 |
| Caprylic acid/capric acid triglyceride | 10.00 |
| Dicaprylyl ether | 5.00 |
| Dimethicone | 2.00 |
| Hydrogenated polyisobutene | 2.00 |
| Vitamin E acetate | 0.50 |
| Ectoin | 1.00 |
| Tinosorb ® S | 1.00 |
| Methylbenzylidenecamphor | 4.00 |
| Titanium dioxide | 1.00 |
| THBC | 0.30 |
| Quercetin | 0.20 |
| Preservative | 0.50 |
| Glycerol | 3.00 |
| Xanthan gum | 0.30 |
| Sodium hydroxide solution, 45% | 0.50 |
| Water | to 100.00 |

EXAMPLE 28

| O/W emulsion | % by wt. |
| --- | --- |
| Sorbitan stearate | 3.00 |
| Polyglyceryl 3-methylglucose distearate | 1.50 |
| Octyldodecanol | 10.00 |
| Dicaprylyl ether | 5.00 |
| Mineral oil | 5.00 |
| Castor oil | 2.00 |
| Butylene glycol dicaprylate/caproate | 5.00 |
| Vitamin E acetate | 0.50 |
| Octocrylene | 8.00 |
| Methylbenzylidenecamphor | 4.00 |
| Butylmethoxydibenzoylmethane | 3.00 |
| THBC sulfate | 0.20 |
| Rutin (water-soluble) | 0.50 |
| Boron nitride | 2.00 |
| 5-Hydroxyectoin | 2.00 |
| Preservative | 0.50 |
| Glycerol | 10.00 |
| Xanthan gum | 0.20 |
| Pemulen ® TR1 | 0.10 |
| Phenylbenzimidazolesulfonic acid | 2.00 |
| Sodium hydroxide solution, 45% | 1.20 |
| Water | to 100.00 |

EXAMPLE 29

| W/O emulsion | % by wt. |
| --- | --- |
| Polyglyceryl 2-dipolyhydroxystearate | 5.00 |
| Dimethicone | 2.00 |
| Mineral oil | 5.00 |
| Isohexadecane | 5.00 |
| Butylene glycol dicaprylate/caproate | 10.00 |
| $C_{12-15}$-Alkyl benzoate | 7.00 |
| Dioctylbutamidotriazone | 3.00 |
| Methylbenzylidenecamphor | 2.00 |
| Butylmethoxydibenzoylmethane | 2.00 |
| Titanium dioxide | 4.00 |
| THBC | 0.20 |
| Rutin (water-soluble) | 0.30 |
| 5-Hydroxyectoin | 0.05 |
| Preservative | 0.50 |
| Glycerol | 5.00 |
| $MgSO_4$ | 1.00 |
| Water | to 100.00 |

EXAMPLE 30

| W/O emulsion | % by wt. |
| --- | --- |
| PEG 30 dipolyhydroxystearate | 4.00 |
| Caprylic acid/capric acid triglyceride | 5.00 |
| Octyldodecanol | 5.00 |
| Dicaprylyl ether | 5.00 |
| Mineral oil | 5.00 |
| Isohexadecane | 2.00 |
| Hydrogenated polyisobutene | 5.00 |
| $C_{12-14}$-Alkyl benzoate | 10.00 |
| Vitamin E acetate | 0.50 |
| Aerosil ® R 972 | 0.50 |
| Ectoin | 5.00 |
| THBC sulfate | 0.20 |
| Rutin (water-soluble) | 0.30 |
| Preservative | 0.50 |
| Glycerol | 10.00 |
| $MgSO_4$ | 1.00 |
| Water | to 100.00 |

EXAMPLE 31

| W/O emulsion | % by wt. |
|---|---|
| Cetyldimethicone copolyol | 5.00 |
| Dimethicone | 5.00 |
| Mineral oil | 2.00 |
| Isohexadecane | 2.00 |
| Butylene glycol dicaprylate/caproate | 5.00 |
| $C_{12-15}$-Alkyl benzoate | 5.00 |
| Tinosorb ® S | 3.00 |
| Octocrylene | 4.00 |
| Methylbenzylidenecamphor | 4.00 |
| Butylmethoxydibenzoylmethane | 2.00 |
| Titanium dioxide | 2.00 |
| THBC | 0.30 |
| Troxerutin | 0.20 |
| Boron nitride | 4.00 |
| 5-Hydroxyectoin | 0.05 |
| Preservative | 0.50 |
| Glycerol | 5.00 |
| NaCl | 1.00 |
| Sodium hydroxide solution, 45% | 1.30 |
| Water | to 100.00 |

EXAMPLE 32

| Hydrodispersion | % by wt. |
|---|---|
| Caprylic acid/capric acid triglyceride | 10.00 |
| Octyldodecanol | 5.00 |
| Dicaprylyl ether | 2.00 |
| Dimethicone | 1.00 |
| Vitamin E acetate | 0.50 |
| Octyltriazone | 2.00 |
| Methylbenzylidenecamphor | 4.00 |
| Butylmethoxydibenzoylmethane | 2.00 |
| Titanium dioxide | 1.00 |
| THBC | 1.00 |
| Troxerutin | 0.20 |
| Ectoin | 5.00 |
| Preservative | 0.50 |
| Glycerol | 3.00 |
| Xanthan gum | 0.40 |
| Pemulen ® TR1 | 0.40 |
| Water | to 100.00 |

EXAMPLE 33

| W/O emulsion | % by wt. |
|---|---|
| Caprylic acid/capric acid triglyceride | 15.00 |
| Hydrogenated polyisobutene | 5.00 |
| $C_{12-15}$-Alkyl benzoate | 5.00 |
| Dioctylbutamidotriazone | 2.00 |
| Octyltriazone | 2.00 |
| Titanium dioxide | 4.00 |
| Aerosil ® R 972 | 2.00 |
| THBC sulfate | 0.50 |
| Troxerutin | 0.20 |
| Boron nitride | 1.00 |
| Ectoin | 1.00 |
| Preservative | 0.50 |
| Glycerol | 5.00 |
| NaCl | 1.00 |
| Water | to 100.00 |

EXAMPLE 34

| Spray | % by wt. |
|---|---|
| Glycerol monostearate | 4.00 |
| Ceteareth-12 | 1.50 |
| Caprylic acid/capric acid triglyceride | 2.00 |
| Mineral oil | 5.00 |
| Octocrylene | 6.00 |
| Ectoin | 0.05 |
| THBC sulfate | 0.20 |
| Preservative | 0.50 |
| Glycerol | 10.00 |
| Phenylbenzimidazolesulfonic acid | 1.00 |
| Sodium hydroxide solution, 45% | 0.40 |
| Water | to 100.00 |

EXAMPLE 35

| Spray | % by wt. |
|---|---|
| Glycerol monostearate SE | 4.50 |
| Ceteareth-20 | 1.00 |
| Dicaprylyl ether | 5.00 |
| Cetylstearyl isononanoate | 5.00 |
| Dimethicone | 2.00 |
| Dioctylbutamidotriazone | 1.00 |
| Tinosorb ® S | 1.00 |
| Ectoin | 1.00 |
| THBC sulfate | 0.10 |
| Boron nitride | 1.00 |
| Preservative | 0.50 |
| Glycerol | 5.00 |
| Water | to 100.00 |

What is claimed is:

1. A cosmetic or pharmaceutical formulation comprising at least one compound of formula I

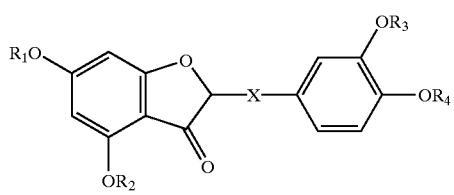

in which

X is a single bond, —$CH_2$—, —C(O)—, —C($NR^5$)—, —CH($NR^5R^6$)—or —CH($OR^5$)—, and $R^1$, $R^2$, $R^3$, $R^4$, $R^5$ and $R^6$, which may be identical or different, are, independently of one another, selected from

H straight-chain or branched $C_1$- to $C_{12}$-alkyl and/or alkylcarbonyl groups, straight-chain or branched $C_3$- to $C_{12}$-alkenyl and/or -alkenylcarbonyl groups, straight-chain or branched $C_1$- to $C_{12}$-hydroxyalkyl groups, in which the hydroxyl group may be bonded to a primary or secondary carbon atom of the chain, and furthermore the alkyl chain may also be interrupted by oxygen, $C_3$- to $C_{10}$-cycloalkyl and/or cycloalkylcarbonyl groups and $C_3$- to $C_{12}$-cycloalkenyl and/or cycloalkenylcarbonyl groups, in which each of the rings may also be bridged by —(CH$_2$)$_n$— groups, where n is 1 to 3, aryl and/or arylcarbonyl groups, heteroaryl and/or heteroarylcarbonyl groups, where these groups may be substituted by alkyl, hydroxyl, alkoxy, amino, mono- and dialkylamino, sulfonic acid, carboxyl and/or halogen groups, mono- and/or oligoglycosyl radicals, and radicals selected from

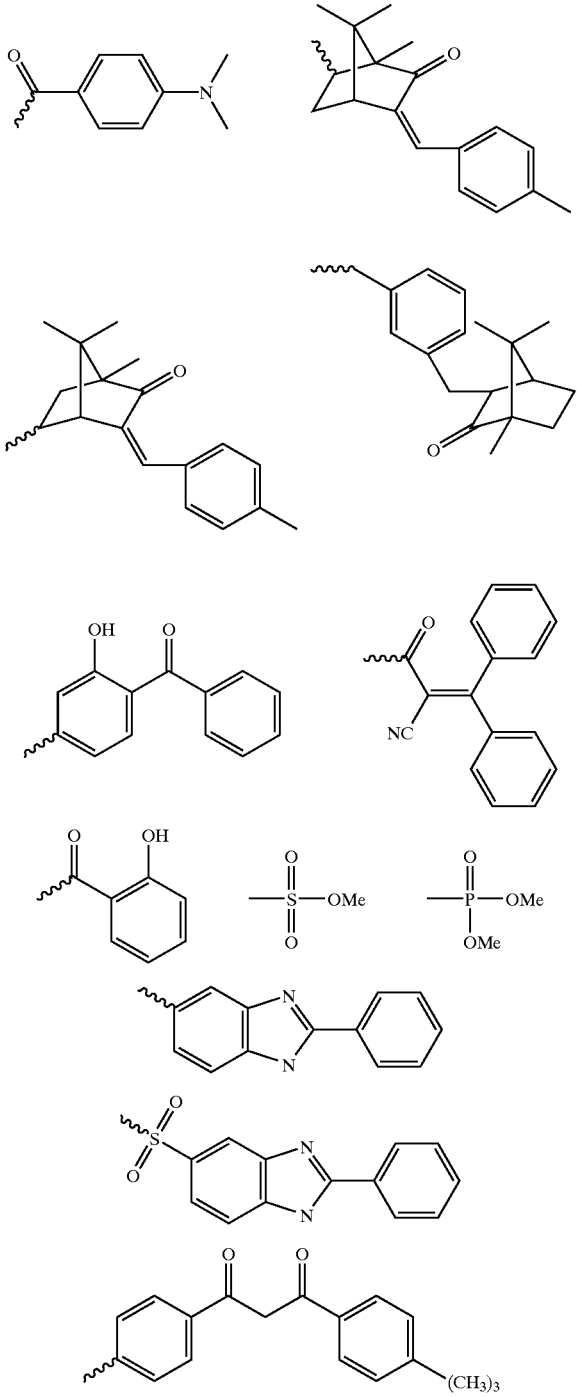
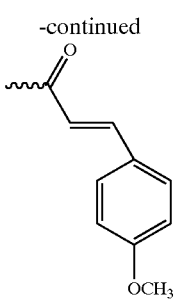
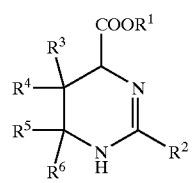

in which Me is a proton or an alkali metal ion.

2. A cosmetic or pharmaceutical formulation according to claim 1, wherein said compound is 4,6,3',4'-tetrahydroxybenzylcoumaran-3-one or 4,6,3',4'-tetrahydroxybenzylcoumaran-3-one trisulfate wherein R$^1$, R$^3$ and R$^4$ are each SO$_3$Me, and R$^2$ is H.

3. A cosmetic or pharmaceutical formulation according to claim 1, wherein said formulation comprises one or more UV filters.

4. A cosmetic or pharmaceutical formulation according to claim 3, wherein said one or more UV filters are selected from 3-(4'-methylbenzylidine)-dl-camphor, 1-(4-tert-butylphenyl)-3-(4-methoxybenzophenone, octyl methoxycinnamate, 3,3,5-trimethycylohexy salicylate, 2-ethylhexyl 4-(dimethylamino)benzoate, 2-ethylhexyl 2-cyano-3,3-diphenylacrylate, and 2-phenylbenzimidazole-5-sulfonic acid and its potassium, sodium and triethanolamine salts.

5. A cosmetic or pharmaceutical formulation according to claim 3, wherein said formulation contains one or more organic UV filters in an amount of 0.5 to 10% by weight.

6. A cosmetic or pharmaceutical formulation according to claim 3, wherein said formulation contains said one or more organic UV filters in an amount of 0.5 to 20% by weight.

7. A cosmetic or pharmaceutical formulation according to claim 1, further comprising one or more antioxidants.

8. A cosmetic or pharmaceutical formulation according to claim 1, further comprising at least one skin-protecting or skin-care active ingredient.

9. A cosmetic or pharmaceutical formulation according to claim 8, wherein said at least one skin-protecting or skin-care active ingredient is an aryl oxime or a pyrimidinecarboxylic acid of formula II

II in which

R$^1$ is a radical H or C$_{1-8}$-alkyl,

R$^2$ is a radical H or C$_{1-4}$-alkyl, and

R$^3$, R$^4$, R$^6$ are each, independently of one another, H, OH, NH$_2$ or C$_{1-4}$-alkyl.

10. A cosmetic or pharmaceutical formulation according to claim 9, wherein said least one skin-protecting or skin-care active ingredient is a pyrimidinecarboxylic acid of formula II wherein R$^2$ is a methyl or ethyl group, and R$^1$ or R$^5$ and R$^6$ are H.

11. A cosmetic or pharmaceutical formulation according to claim 9, wherein said at least one skin-protecting or skin-care active ingredient is 2-hydroxy-5-methyllaurophenone oxime.

12. A cosmetic or pharmaceutical formulation according to claim 10, wherein said at least one of said skin-protecting or skin-care active ingredient is (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid.

13. A cosmetic formulation according to claim 9, wherein said formulation contain a pyrimidinecarboxylic acid of formula II in an amount of up to 15% by weight.

14. A cosmetic formulation according to claim 9, wherein said formulation contains an aryl oxime in an amount of 0.01 to 10% by weight.

15. A cosmetic or pharmaceutical formulation according to claim 1, further comprises at least one O/W or W/O emulsifiers and said formulation is an emulsion.

16. A cosmetic or pharmaceutical formulation according to claim 15, wherein said formulation comprises at least one W/O emulsifier selected from glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2)stearyl ether (steareth-2), glyceryl monolaurate, glyceryl monocaprinate, and glyceryl monocaprylate.

17. A cosmetic or pharmaceutical formulation according to claim 1, further comprising at least one hydrophilic surfactant.

18. A cosmetic or pharmaceutical formulation according to claim 17, wherein said at least one hydrophilic surfactant is selected from alkyl glycosides, acyl lactylates, betaines and coconut amphoacetates.

19. A cosmetic formulation according to claim 17, wherein said formulation contains 0.01–20% by weight of said at least one hydrophilic surfactant.

20. A cosmetic or pharmaceutical formulation according to claim 1, wherein Me is a sodium or potassium ion.

21. A cosmetic or pharmaceutical formulation according to claim 1, wherein at least one of the radicals $R^1$, $R^2$, $R^3$ and $R^4$ is a mono-or oligosaccharide.

22. A cosmetic or pharmaceutical formulation according to claim 1, wherein at least one of the radicals $R^1$, $R^2$, $R^3$ and $R^4$ contains a ramnosyl, glycosyl, allosyl, altrosyl, galactosyl, gulosyl, idosyl, mannosyl or talosyl radical.

23. A cosmetic or pharmaceutical formulation according to claim 1, wherein said formulation contains 0.01–10% by weight of said compound of formula I.

24. A cosmetic of pharmaceutical formulation according to claim 1, wherein formulation contains 0.02–5% by weight of said compound of formula I.

25. A cosmetic of pharmaceutical formulation according to claim 1, wherein said formulation contains 0.05–0.2% by weight of said compound of formula I.

26. A cosmetic formulation according to claim 1, further comprising one or more vitamins selected from vitamins selected from vitamin A, vitamin A propionate, vitamin A palmitate, vitamin A acetate, retinol, vitamin B, thiamine chloride hydrochloride, riboflavin, nicotinamide, vitamin C, vitamin D, ergocalciferol, vitamin E, DL-α-tocopherol, tocopherol E acetate, tocopherol hydrogen-succinate, vitamin $K_1$, esculin, thiamine, nicotinic acid, pyridoxine, pyridoxal, pyridoxamine, panthothenic acid, biotin, folic acid and cobalamine.

27. A cosmetic formulation according to claim 26, wherein the ratio of vitamins to compounds of the formula I in the ratios is 100:1 to 1:100.

\* \* \* \* \*

UNITED STATES PATENT AND TRADEMARK OFFICE
CERTIFICATE OF CORRECTION

PATENT NO. : 6,903,134 B2
DATED : June 7, 2005
INVENTOR(S) : Frank Pfluecker

It is certified that error appears in the above-identified patent and that said Letters Patent is hereby corrected as shown below:

Column 40,
Line 52, reads "-CH($NR^5R^6$)-or" should read -- -CH($NR^5R^6$)- or --.

Column 42,
Line 26, reads "(4-methoxybenzophenone," should read -- (4- methoxyphenyl)propane-1,3-dione, 4-isopropyldibenzoylmethane, 2-hydroxy-4-methoxybenzophenone, --.
Line 27, reads "trimethycylohexy" should read -- trimethylcyclohexyl --.
Line 60, reads "$R^3$, $R^4$, $R^6$ are each" should read -- $R^3$, $R^4$, $R^5$ and $R^6$ are each --.
Line 63, reads "wherein said least" should read -- wherein said at least --.

Column 43,
Line 6, reads "to claim 10," should read -- to claim 9, --.
Line 12, reads "said formulation contain" should read -- said formulation contains --.
Line 18, reads "further comprises" should read -- further comprising --.
Line 19, reads "emulsifiers and said formulation" should read -- emulsifier and said formulation --.
Line 27, reads "sorbitan monoistearate," should read -- sorbitan monoisostearate, --.

Column 44,
Line 10, reads "mono-or" should read -- mono- or --.
Lines 18 and 21, reads "cosmetic of pharmaceutical" should read -- cosmetic or pharmaceutical --.
Line 19, reads "wherein formulation" should read -- wherein said formulation --.
Line 25, reads "vitamins selected from vitamins selected" should read -- vitamins selected --.
Line 36, reads "I in the ratios is" should read -- I is --.

Signed and Sealed this

Seventh Day of February, 2006

JON W. DUDAS
*Director of the United States Patent and Trademark Office*